US010031149B2

(12) United States Patent
Lapham et al.

(10) Patent No.: US 10,031,149 B2
(45) Date of Patent: Jul. 24, 2018

(54) ROBOTIC SYSTEM FOR SORTING SAMPLE TUBES

(71) Applicant: Counsyl, Inc., South San Francisco, CA (US)

(72) Inventors: Kyle Lapham, South San Francisco, CA (US); Ethan Nash, South San Francisco, CA (US); Peter Turner, South San Francisco, CA (US); Kevin Haas, South San Francisco, CA (US); Christopher Wong, South San Francisco, CA (US)

(73) Assignee: Counsyl, Inc., South San Francisco, CA (US)

( * ) Notice: Subject to any disclaimer, the term of this patent is extended or adjusted under 35 U.S.C. 154(b) by 11 days.

(21) Appl. No.: 15/388,193

(22) Filed: Dec. 22, 2016

(65) Prior Publication Data

US 2017/0190056 A1    Jul. 6, 2017

Related U.S. Application Data

(60) Provisional application No. 62/274,133, filed on Dec. 31, 2015, provisional application No. 62/301,365, filed on Feb. 29, 2016.

(51) Int. Cl.
| | |
|---|---|
| *G01N 35/00* | (2006.01) |
| *B25J 19/04* | (2006.01) |
| *B25J 15/06* | (2006.01) |
| *B25J 9/04* | (2006.01) |
| *B25J 19/02* | (2006.01) |
| *G01N 35/04* | (2006.01) |

(52) U.S. Cl.
CPC .......... *G01N 35/0099* (2013.01); *B25J 9/042* (2013.01); *B25J 15/0658* (2013.01); *B25J 19/023* (2013.01); *G01N 35/00732* (2013.01); *G01N 2035/00851* (2013.01); *G01N 2035/0493* (2013.01)

(58) Field of Classification Search
CPC .................. G01N 35/00732; G01N 35/0099
See application file for complete search history.

(56) References Cited

U.S. PATENT DOCUMENTS

| | | | | |
|---|---|---|---|---|
| 4,947,702 | A | 8/1990 | Kato | |
| 5,357,095 | A * | 10/1994 | Weyrauch | G01N 35/00663 235/375 |
| 7,282,361 | B2 * | 10/2007 | Hodge | C12Q 1/6834 435/183 |
| 8,535,624 | B2 | 9/2013 | Luoma | |
| 8,703,492 | B2 * | 4/2014 | Self | G01N 35/04 422/63 |
| 9,250,229 | B2 | 2/2016 | Holmes | |
| 2003/0088963 | A1 * | 5/2003 | Mayer | B01D 61/18 29/426.5 |

(Continued)

OTHER PUBLICATIONS

PCT/US16/68337 International Search Report, dated Aug. 3, 2017.

(Continued)

*Primary Examiner* — Thomas Randazzo
(74) *Attorney, Agent, or Firm* — FisherBroyles, LLP; Jill A. Jacobson; Victoria Boyd

(57) ABSTRACT

A robotic system is provided for accurately and quickly sorting sample tubes within or between sample tube racks.

32 Claims, 18 Drawing Sheets

(56) References Cited

U.S. PATENT DOCUMENTS

| | | | |
|---|---|---|---|
| 2008/0116338 A1* | 5/2008 | Kalb | B25J 15/0616 |
| | | | 248/205.9 |
| 2009/0239233 A1* | 9/2009 | Hunkapiller | G01N 35/00732 |
| | | | 435/6.18 |
| 2011/0181875 A1* | 7/2011 | Nakahana | B01L 3/5082 |
| | | | 356/246 |
| 2012/0107793 A1 | 5/2012 | Tatsutani | |
| 2013/0041509 A1* | 2/2013 | Saito | B25J 9/06 |
| | | | 700/261 |
| 2015/0079684 A1 | 3/2015 | Bucher et al. | |
| 2017/0045542 A1* | 2/2017 | Lapham | G01N 35/026 |

OTHER PUBLICATIONS

Thermo Scientific Nautilus LIMS: Delivering Data Management and Workflow Solutions for Genomics, Cinical Diagnostics, R&D and Biorepository Laboratories, 2016, Thermo Scientific.
Thermo Scientific Nautilus LIMS: Delivering Lab-Centric Solutions for Patient-Centric Results, 2016, Thermo Scientific.
BioMicroLab, XL9 Tube Handler, 2004-2016.

\* cited by examiner

ROBOTIC SYSTEM FOR SORTING SAMPLE TUBES

CROSS-REFERENCE TO RELATED APPLICATIONS

This application claims the benefit of U.S. Provisional Application No. 62/274,133, filed on Dec. 31, 2015, and U.S. Provisional Application No. 62/301,365, filed on Feb. 29, 2016, both of which are incorporated herein by reference in their entireties.

FIELD OF THE INVENTION

The invention relates to a robotic system for sorting of sample tubes, in particular a system for sorting uniquely coded sample tubes to desired locations for processing operations and analysis of the samples.

BACKGROUND

Samples that are obtained from individual are often processed or analyzed in many different operations or diagnostic tests. Samples from many individuals may be conveniently contained in sample tubes that are stored in a sample tube rack. The tubes may then be sorted for downstream analytical or processing operations which may be different for each sample. Sorting tubes by hand is cumbersome, time consuming, and error prone. Mechanical grippers for moving sample tubes from one location to another include parts that can wear out, require complicated construction and control mechanisms, and may cause increased wear on the sample tubes. Moreover, coded information on the sample tubes may be read one tube at a time, as the gripper passes the tube within view of a code reading instrument, which is time consuming.

There is a need for a system that can sort uniquely coded sample tubes rapidly and accurately from one location in a sample tube rack to another location for use in a desired analytical or processing operation, and in which coded information on a large number of sample tubes, such as an entire sample tube rack, may be read without moving tubes individually into proximity of a code reader.

BRIEF SUMMARY OF THE INVENTION

Devices and methods are provided for sorting sample tubes.

In one aspect, a device is provided that includes: a robotic assembly, including: a base that includes a vertical lift shaft; a horizontal robotic arm including a proximal end and a distal end, wherein the proximal end of the robotic arm is configured to be lifted vertically by the lift shaft and is configured for pivotal movement around the base; and end of arm tooling at the distal end of the robotic arm that is configured to pick up and hold a sample tube when a vacuum is applied and to expel and deposit the sample tube into a designated slot in a tube rack when air is expelled through the tooling; a vacuum source that is fluidly connected to the end of arm tooling and configured to pull a vacuum through the tooling; an air source that is fluidly connected to the end of arm tooling and configured to expel air through the tooling; a horizontal stage underneath the robotic arm and configured to hold a plurality of tube racks in a position from which the end of arm tooling may pick up and deposit sample tubes; a vision system that is configured to record coded information on sample tubes and on the sides of tube racks in the device and to convey the coded information to a control system; and a control system that tracks coded information provided by the vision system, and that controls the robotic assembly to pick up a coded sample tube from a first location in a first tube rack and to deposit the sample tube in a second location in a second tube rack, wherein the first tube rack and the second tube rack are the same or different.

In some embodiments, the device may further include a plurality of sample tubes in one or more tube racks, wherein each sample tube includes a unique identification code that may be read by the vision system and conveyed to the control system. In some embodiments, the device may further include a plurality of tube racks, wherein each tube rack includes a unique identification code that may be read by the vision system and conveyed to the control system. In some embodiments, the coded information includes one-dimensional, two-dimensional, or three-dimensional bar codes on sample tubes and/or on tube racks.

In some embodiments, the robotic arm is a Selective Compliance Assembly Robot Arm (SCARA), e.g., including: a first horizontal arm segment including: a first proximal end that is configured to be lifted by the lift shaft and is configured for pivotal movement around the base, and a first distal end; a second horizontal arm segment including: a second proximal end that is rotatably coupled to the first distal end, and a second distal end; a third horizontal arm segment including: a third proximal end that is rotatably coupled to the second distal end, and a third distal end; and the end of arm tooling connected to the third distal end.

In some embodiments, the end of arm tooling includes: an open column including a top and a bottom, extending through at least a portion of the interior of the tooling and through which a suction force is applied via the vacuum source and air is expelled via the air source; a first fitting that is connected to the top of the column and that is fluidly connected to the vacuum source and to the air source; an adaptor at the bottom of the column that is of a dimension suitable to connect with and retain the top of a sample tube by suction when a vacuum is applied; an open chamber including a top and a bottom, located within an upper portion of the tooling, wherein the chamber surrounds the first fitting; and a second fitting that is fluidly connected to the air source and through which air passes into the top of the chamber when air pressure is applied, wherein the bottom of the chamber includes a plurality of openings through which air passes when air pressure is applied, said openings extending through a lower portion of the tooling and configured to expel air through the bottom of the tooling when the device is in operation. In an embodiment, the plurality of openings is a ring of openings around the open column that extends through the interior of the tooling and that are configured to expel air around a sample tube, preventing interference from surrounding tubes in the tube rack, if any, when the robotic arm picks up the sample tube. In an embodiment, the ring of openings is disposed in a substantially circular configuration around the open column, and is configured to expel air in a substantially circular configuration around a sample tube.

In some embodiments, the vacuum source and the air source run simultaneously, a vacuum is pulled through the end of arm tooling through the open column when a sample tube is picked up, the vacuum is shut off when the sample tube is above a desired location in a tube rack, and air is expelled briefly through the column after the vacuum is shut off, depositing the sample tube into the desired location in the tube rack.

In some embodiments, the device includes at least one sample tube rack that includes sample tubes, wherein each sample tube in the rack includes unique coded information on the bottom of the tube, wherein the tube rack includes openings such that the coded information on the sample tubes is viewable through the bottom of the tube rack, wherein the vision system is configured beneath the bottom of the tube rack, and wherein the vision system records the locations of coded information when the tube rack is positioned above the vision system. In some embodiments, the device includes at least one sample tube rack that includes unique coded information on at least one side, wherein the sample tube rack and the vision system are configured such that the coded information is recorded by the vision system when the tube rack is positioned above the vision system.

In some embodiments, the vision system includes three vision camera systems that are aligned to read coded information from a sample tube or sample tube rack when it is located in a position above the vision system. In an embodiment, the device includes a vision system under each location on the stage on which a sample tube rack may be positioned. In another embodiment, the device includes a single vision system, and includes a track to move sample tube racks into position above the vision system for reading of coded information on sample tubes and/or on the tube rack.

In some embodiments, the device includes a sample tube rack including a plurality of sample tubes to be sorted, wherein each sample tube includes a top and a bottom, wherein the top of the tube is configured and of a dimension such that the tube will be held by suction when picked up by the end of arm tooling of the robotic arm when a vacuum is applied therethrough, and wherein each sample tube comprises unique coded information on the bottom of the tube, wherein the vision system is configured to read and convey information about the locations of the coded information to the control system before and after sorting to desired locations in one or more tube rack.

In some embodiments, the vacuum source and the air source are produced with a vacuum pump that creates a vacuum through the venturi effect, wherein a vacuum is produced when compressed air flows through a venturi, and wherein positive air pressure is produced when the flow of compressed air is terminated.

In some embodiments, the device further includes a tube sensor that senses whether a sample tube has been picked up by the end of arm tooling when the vacuum is applied.

In some embodiments, the stage is in the form of a deck or a track on a conveyer belt.

In some embodiments, the device is configured to sort 20, 30, or 40, or more sample tubes per minute.

In another aspect, a method is provided for sorting sample tubes, including a device as described herein, and further including at least one sample tube rack that includes sample tubes, wherein a sample tube in a first location is sorted to a second location on the same or different sample tube rack, wherein the control system moves the robotic arm to configure the end of arm tooling above the first location, wherein a vacuum is applied via the vacuum source, thereby providing a suction force through the end of arm tooling, wherein the sample tube is picked up from the first location and retained by the end of arm tooling via vacuum suction, wherein the control system moves the robotic arm to configure the end of arm tooling with the retained sample tube above the second location, wherein the vacuum is terminated and positive air pressure is applied through the end of arm tooling to expel the sample tube in the second location, and wherein the presence of the sample tube in the first location and/or second location is determined by reading of coded information on the sample tube by the vision system.

In some embodiments, the control system lowers the robotic arm before the sample tube is picked up, raises the robotic arm when it is moved to configure the end of arm tooling above the second location, and lowers the robotic arm before the sample tube is expelled in the second location.

In an embodiment, the robotic arm is a SCARA, including: a first horizontal arm segment, including: a first proximal end that is configured to be lifted by the lift shaft and is configured for pivotal movement around the base, and a first distal end; a second horizontal arm segment including: a second proximal end that is rotatably coupled to the first distal end, and a second distal end; a third horizontal arm segment including: a third proximal end that is rotatably coupled to the second distal end, and a third distal end; and the end of arm tooling connected to the third distal end.

In some embodiments, the end of arm tooling includes: an open column including a top and a bottom, extending through at least a portion of the interior of the tooling and through which a suction force is applied via the vacuum source and air is expelled via the air source; a first fitting that is connected to the top of the column and that is fluidly connected to the vacuum source and to the air source; an adaptor at the bottom of the column that is of a dimension suitable to connect with and retain the top of a sample tube by suction when a vacuum is applied; an open chamber comprising a top and a bottom, located within an upper portion of the tooling, wherein the chamber surrounds the first fitting; and
a second fitting that is fluidly connected to the air source and through which air passes into the top of the chamber when air pressure is applied, wherein the bottom of the chamber includes a plurality of openings through which air passes when air pressure is applied, said openings extending through a lower portion of the tooling and configured to expel air through the bottom of the tooling when the device is in operation. In an embodiment, the plurality of openings is a ring of openings around the open column that extends through the interior of the tooling, wherein air is expelled around a sample tube, preventing interference from surrounding tubes in the tube rack, if any, when the robotic arm picks up the sample tube. In an embodiment, the ring of openings is disposed in a substantially circular configuration about the open column, and air is expelled in a substantially circular configuration around the sample tube.

In some embodiments, the vacuum source and air source run simultaneously, wherein a vacuum is pulled through the end of arm tooling through the open column when a sample tube is picked up, wherein the vacuum is shut off when the sample tube is above a desired location in a tube rack, and wherein air is expelled briefly through the column after the vacuum is shut off, depositing the sample tube into the desired location in the tube rack. In an embodiment, the vacuum source and the air source are produced with a vacuum pump that creates a vacuum through the venturi effect, wherein a vacuum is produced when compressed air flows through a venturi, providing a suction force whereby the sample tube is picked up from the first location, and wherein positive air pressure is produced when the flow of compressed air is terminated, thereby expelling the sample tube in the second location.

In some embodiments, the coded information includes one-dimensional, two-dimensional, or three-dimensional bar codes on sample tubes and/or on sample racks. In an embodiment, each sample tube in the tube rack includes unique coded information on the bottom of the tube, wherein the tube rack includes openings such that the coded information on the sample tubes is viewable through the bottom of the tube rack, wherein the vision system is configured beneath the bottom of the tube rack, and wherein the vision system records the locations of coded information when the tube rack is positioned above the vision system. In an embodiment, each sample tube rack includes unique coded information on at least one side, wherein the sample tube rack and the vision system are configured such that the coded information is recorded by the vision system when the tube rack is positioned above the vision system.

In some embodiments, the vision system includes three vision camera systems that are aligned to read coded information from a sample tube or sample tube rack when it is located in a position above the vision system.

In some embodiments, the device further includes a tube sensor that senses whether a sample tube has been picked up by the end of arm tooling when the vacuum is applied.

In some embodiments, the device is configured to sort 20, 30, or 40, or more sample tubes per minute.

DETAILED DESCRIPTION

Figure 1:
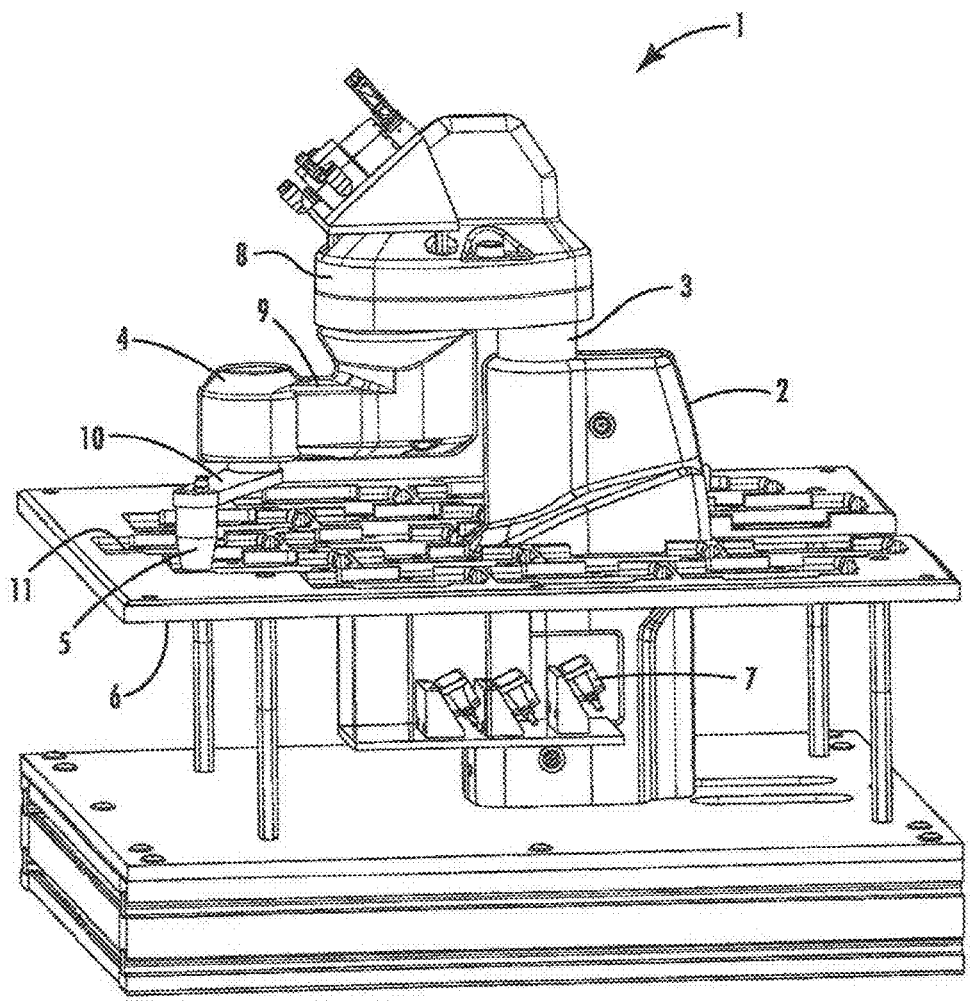
FIG. 1 shows an embodiment of a sample tube sorting device.

The invention provides methods and devices for sorting sample tubes. The methods and devices disclosed herein include a robotic assembly with a robotic arm that may be lifted and lowered and that is configured to pivot around a base. Sample tubes are picked up by applying a vacuum such that tubes are picked up by suction and retained by end of arm tooling on the robotic arm. A sample tube is picked up by vacuum suction, the robotic arm moves the tube into position above a desired location, and the tube is deposited in the desired location by shutting off the vacuum and expelling a brief burst of air through the end of arm tooling to release the sample tube.

In some embodiments, a vacuum source and air source run simultaneously while the tube is retained on the end of arm tooling, and when the vacuum shuts off, a "puff" of air pushes the tube into the desired location. For example, the vacuum source and the air source may be produced with a vacuum pump that creates a vacuum through the venturi effect, producing a vacuum as compressed air flows through a venturi, thereby providing a suction force for picking up and retaining a sample tube. A brief burst of positive air pressure is produced when the flow of compressed air is terminated, thereby expelling the sample tube in a desired location.

In some embodiments, air is expelled through a plurality of openings that extend through a lower portion of the end of arm tooling and that surround the sample tube as it is being picked up by the tooling, holding surrounding tubes in a tube rack in place, pushing them out of the way so that they do not interfere with picking up of the tube that is to be sorted to another location. Such an embodiment may improve reliability of sorting, by improving accuracy of picking up the sample tube of interest without interference by surrounding tubes in the tube rack.

Sample tubes to be sorted as disclosed herein include unique coded identifying information. The unique coded information on sample tubes permits compilation of data from different analytical or process operations for an individual from whom the sample was obtained. Sorting operations are dynamic and may be tailored for the analytical or diagnostic needs of the individual. Sample tubes may be moved into position for a downstream test or processing operation based on information obtained from an upstream test or operation. In some embodiments, unique identification codes are present on the bottoms of sample tubes and the sample sorting device includes a vision system that may read the codes on the bottoms of tubes of an entire sample tube rack, conveying the information to a control system. In some embodiments, the device contains a plurality of sample tube racks, each of which contains a unique identification code, such that tubes are sorted to coded tube racks, i.e., each uniquely coded sample tube may be sorted to a desired location in a uniquely coded sample tube rack (e.g., a sample tube rack that contains uniquely coded information along one or more length and/or width sides(s) of the tube rack). Coded sample tubes may be scanned before and after sorting, and optionally a sensor may be deployed to sense whether a sample tube has been picked up by the device, e.g., by monitoring air pressure. Such scanning and sensing reduces errors and improves reliability. Accuracy of sorting is of critical importance, particularly for clinical samples and diagnostic operations.

Sample tubes may be sorted as disclosed herein at a speed of greater than 10, 20, 30, or 40 sample tubes per minute.

A "sample tube" may refer to a sample collection test tube or other container ("primary tube"), which is used to receive a sample, for example, a sample that is obtained from an individual such as a patient, and may be used to transport the sample to a location at which analytical or diagnostic procedures may be performed on the sample. A "sample tube" may also refer to a secondary sample tube or container ("secondary tube") into which an aliquot of the sample from the primary tube is transferred, for example, of a convenient size or configuration for analytical or diagnostic procedures that will be performed on the sample therein. A sample tube may be constructed of glass or plastic or other suitable material for containing a sample of interest, has a closed end and an open end, with the open end closed or capped with a closure. In some embodiments, the closure at the open end of the sample tube contains a septum through which at least a portion of the sample in the tube may be withdrawn. In other embodiments, the closure may contain a screw type or hinged lid. A sample tube may be, for example, a tubular test tube which may, for example, contain a cylindrical shaft closed on the bottom by a rounded (e.g., hemispherical) or conical, bottom. A tubular test tube may have a generally round profile as sectioned perpendicular to the shaft axis.

A "sample" may include, but is not limited to, blood, plasma, saliva, urine, semen, oocytes, skin, hair, feces, cheek swabs, or pap smear lysate from an individual.

A "tube rack" refers to a tube holder with a plurality of slots for holding sample tubes. The tube rack is typically configured to hold sample tubes in an upright manner.

"Coded information" or "identification code" refers to information that can be retrieved to identify a sample, the source of a sample, and/or information about a sample (e.g., a patient from whom a sample was obtained, a tissue source, etc.). Coded information may, for example, be in the form of a one-dimensional, two-dimensional, or three-dimensional barcode.

Sample tube sorting devices disclosed herein include a robotic arm for picking up a sample tube from a first location in a first sample tube rack and sorting the tube to a second location in the first sample tube rack or in a second sample tube rack. The initial loading of sample tubes in the first tube rack may be manual or may utilize a second robotic arm, e.g., including an interface between another robotic system and the sample tube sorting device. Use of a robotic system as disclosed herein improves speed of sorting, permitting, for example, sorting of greater than 10, 20, 30, or 40 sample tubes per minute.

In some embodiments, the robotic arm is a Selective Compliance Assembly Robot (SCARA), containing a plurality of independently movable horizontal or substantially horizontal arm segments, with end of arm tooling containing an adaptor for picking up and retaining a sample tube of desired dimensions. Different size tubes may be sorted by changing the adaptor on the end of arm tooling. In some embodiments, the device may include the ability to change the end of arm tooling and/or tube retention adaptor itself. The arm segments are rotatably coupled to each other, and the device includes a lift shaft between the base of the device and the first arm segment, for lifting and lowering the arm relative to the sample tubes and sample tube racks. The lift shaft permits pivotal movement of the robotic arm around the base. The multiple, independently rotatable arm segments permit greater maneuverability to move the end of arm tooling into position for picking up and depositing sample tubes and improve speed of sorting.

In operation, the robotic arm positions the end of arm tooling above a sample tube to be sorted, the arm is lowered to permit the tube to be picked up and retained by the end of arm tooling by vacuum suction, the arm is raised to move the tube to a desired location, the arm is lowered, the vacuum is terminated, and a short burst or puff of positive air pressure pushes the sample tube into the desired location, e.g., a desired slot in a sample tube rack. Using air pressure to release the tube increases reliability, versus simply turning off the vacuum and releasing the tube. The puff of air is released quickly and the air spreads out from the terminal opening through the tube retention adaptor on the end of arm tooling, increasing accuracy for deposit of the tube in the desired location.

In some embodiments, a sensor determines whether the sample tube has been picked up. If not, the device may be programmed to try to pick up the tube again, for example, for a set length of time. If the tube is not picked up, the system may send a message notifying an operator of the failure to pick up and sort the tube.

Sample tube racks may be positioned around the robotic device in proximity to the robotic arm within reach of the end of arm tooling. In some embodiments, the sample tube racks are positioned on a stage, for example, a deck or a track on a conveyer belt.

The sample tube sorting devices disclosed herein include a vision system, for reading and conveying coded information on sample tubes and tube racks to a control system. The vision system may include, for example, one or more high speed camera. After sorting, reading of the coded information provides validation that the right tube has been picked up and deposited in the right location. In some embodiments, the vision system includes one, two or three cameras, configured to read coded information on all tubes in a filled sample tube rack and coded information on the side of the tube rack. A vision system may be configured underneath each sample tube rack on a stage, or one or more vision system(s) may be configured such that either the vision system moves or the sample tube rack moves to position sample tube racks above the vision system. In some embodiments, the vision system is configured such that a mirror is not necessary for reading coded information on sample tubes or tube racks.

The sample tube sorting devices disclosed herein include a control system. The control system may be internal or external to the sorting device, and in some embodiments, may be separated by some distance. The connection between the control system and the sample tube sorting device may be, for example, via cables or wireless transmission. In some embodiments, the sample tube sorting device is attached to one or more computer(s) that receives instructions for sample sorting and conveys the instructions to the sorting device for implementation.

The control system may control one or more function(s) related to sample tube sorting, as described herein, including, but not limited to movement of the robotic arm in a path within sample tube racks, movement of the robotic arm in a path between sample tube racks, reading and tracking of unique coded information on sample tubes and/or on sample tube racks, and picking up and depositing of sample tubes in desired locations. In some embodiments, the control system may control movement of sample tubes according to a predetermined schedule. In some embodiments, the control system may control or interface with another control system that controls one or more liquid handling, analytical, or processing functions related to samples in the sample tubes, including but not limited to, dispensing of liquid, aspiration of liquid, detection of a signal, or extraction of biomolecule(s).

In some embodiments, a control system may be configured to control one or a plurality of sample tube sorting devices, and optionally, one or a plurality of sample liquid handling systems or other devices or systems for processing or analyzing samples in the sample tubes.

In some embodiments, a sample tube sorting device, as disclosed herein, may be connected to or interface with one or more device(s) or system(s) for processing samples in the sample tubes. For example, tubes may be sorted and moved to a device or system for processing of the sample, extraction of a material, such as one or more biomolecule(s) from the sample, or analytical or diagnostic testing on the sample, and after such downstream operation has been performed, the sample tubes may be returned to the sample tube sorting device for resorting or removal.

In some embodiments, a sample tube sorting device, as disclosed herein, may include capabilities and hardware for one or more sample processing operations, including, but not limited to, extraction of a material, such as one or more biomolecule(s) from the sample, or analytical or diagnostic testing on the sample. For example, the end of arm tooling may be changed from tooling for sorting sample tubes to hardware for performing sample processing operations. In some embodiments, the changing of end of arm tooling may be robotically automated and controlled by the control system.

In some embodiments, a sample tube sorting device as described herein batches samples, e.g., patient samples, for various assays or other treatments or tests. For example, from a large number of samples, certain samples that are desired to be assayed in a first assay are sorted to a first sample tube rack. Optionally, other samples that are desired to be assayed in a second assay may be sorted to a second sample tube rack. Some of the tubes in the first and/or second sample tube racks may be sorted to a third sample tube rack for a third assay, for example, dependent on the results obtained in the first and/or second assay. Sample tubes are pre-batched, i.e., pre-sorted prior to assay, rather than batched as the assay destination. The batch is created at a specific sorting point and then sent together for assay, and then all or a portion of the sample tubes may be resorted for further assay(s) or returned to their starting locations. Control samples may be included in the pre-sorted sample tube rack, rather than assayed separately from samples. Controls may be sorted to any desired location within a sample tube rack.

Based on the results of one assay or test procedure, each sample tube may be sorted to additional assay(s) or test(s), may be re-run in the same assay(s) or test(s), or may be returned to a starting or storage location. The sample tube sorting device herein may operate as a continuous flow sorting system, with a high ratio of input to output, permitting storage of less samples than a compound management system.

Exemplary Embodiments

The following embodiments are intended to illustrate, but not limit, the invention.

Figure 2:
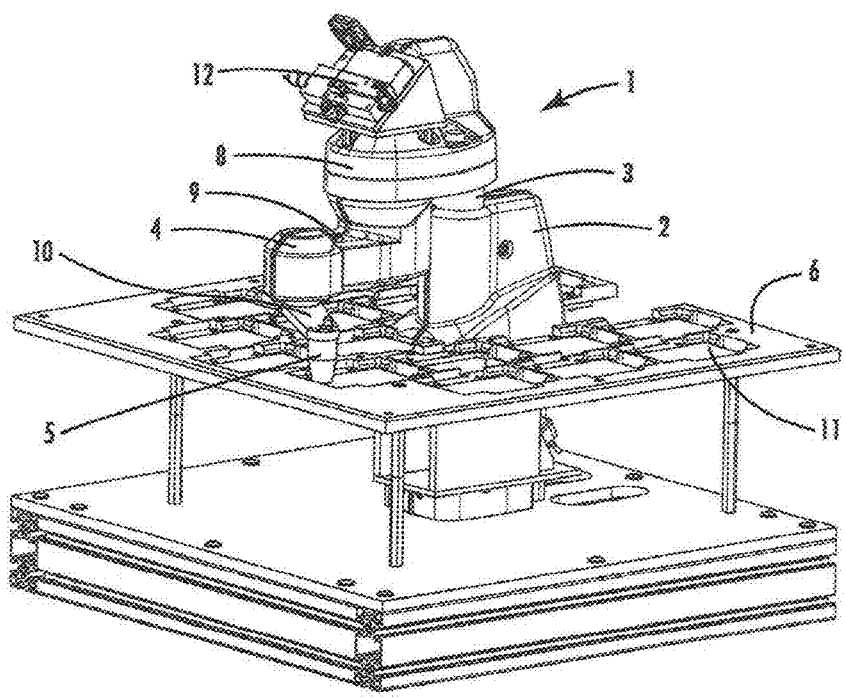
FIG. 2 shows a perspective view of an embodiment of a sample tube sorting device.

FIGS. 1 and 2 show an embodiment of a sample tube sorting device as described herein. The sample sorting device includes a robotic assembly 1, with a base 2, a vertical shaft 3 that can lift and lower a robotic arm 4 that includes end of arm tooling 5 that can pick up and deposit sample tubes in desired locations in sample tube racks that are positioned on a horizontal stage 6. In the embodiment depicted in FIG. 1, the stage contains slots or fittings 11 to retain sample tube racks, disposed in a horizontal or substantially horizontal configuration about the robotic assembly. The sample sorting device also includes a vision system 7, configured to view and record coded information on sample tubes and on the sides of sample tube racks in the device, and to convey the coded information to a control system.

In the device depicted in FIGS. 1 and 2, the robotic arm includes a first arm segment 8 that is coupled at its proximal end to shaft 3, configured to be lifted and lowered by the shaft, and configured for pivotal movement about the base 2. The first arm segment is coupled at its distal end to the proximal end of a second arm segment 9, and the second arm segment is coupled at its distal end to the proximal end of a third arm segment 10. The third arm segment contains end of arm tooling 5 at its distal end, configured to pick up a sample tube when a vacuum is applied and to expel the sample tube in a desired location when air is expelled through the tooling. The second and third arm segments are capable of independent rotation about vertical or substantially vertical axes of rotation. The shaft 3 moves the robotic arm down to pick up a tube, moves the robotic arm up after the tube has been acquired and is held in place by vacuum, and moves the tube back down after the arm has moved the end of arm tooling into the location above a desired slot in a sample tube rack into which the tube will be deposited when air is expelled through the tooling.

Figure 3:
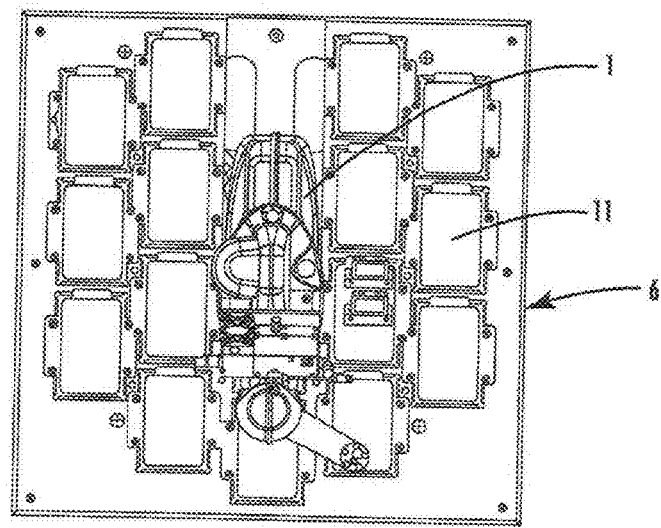
FIG. 3 shows a plan view of an embodiment of a sample tube sorting device.

FIG. 3 depicts a plan view of an embodiment of a sample tube sorting device, as seen from above. Horizontal stage 6 surrounds robotic assembly 1 and contains slots or fittings 11 for positioning of sample tube racks about the robotic device and within the reach of the robotic arm and end of arm tooling, for picking up and depositing sample tubes therein.

Figure 4:
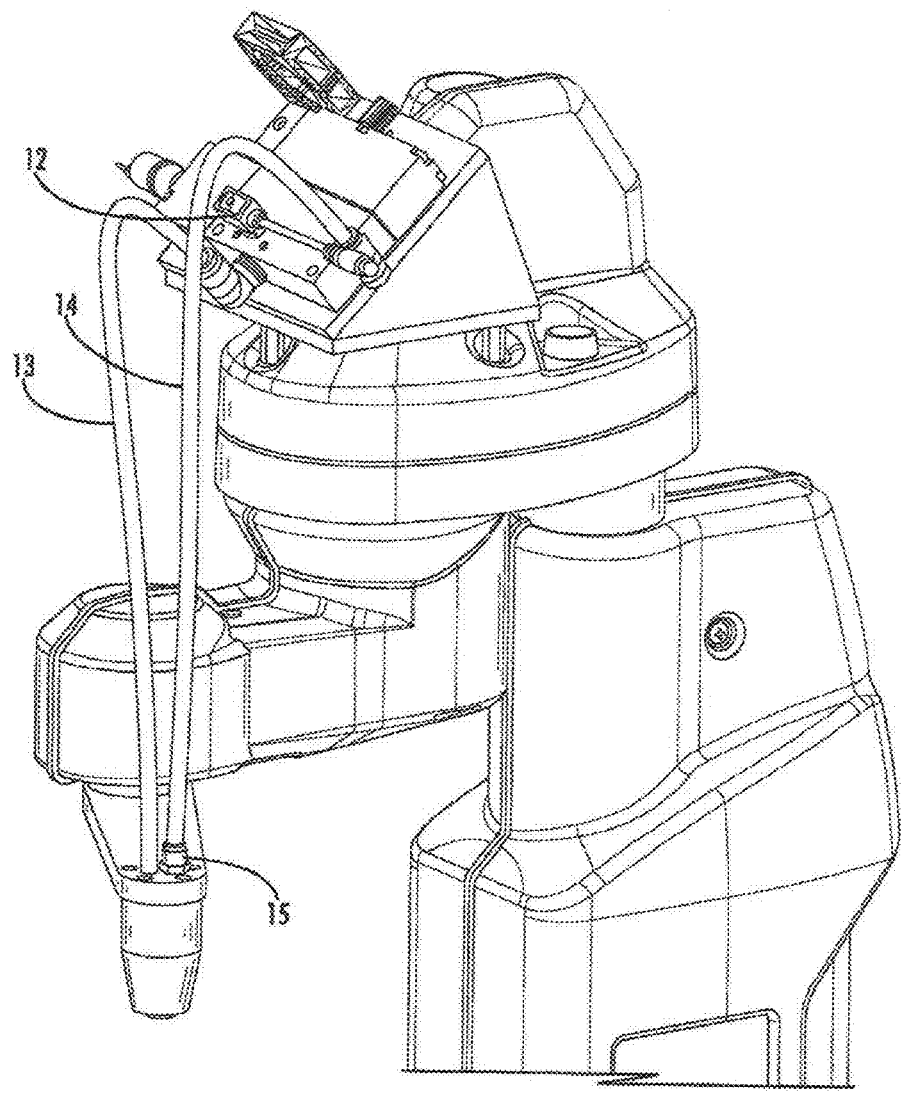
FIG. 4 shows an embodiment of a robotic arm of a sample tube sorting device

FIG. 4 depicts an embodiment of a sample sorting device as described herein, containing a vacuum source that is fluidly connected to the end of arm tooling of the robotic arm through tubing 13, and an air source that is fluidly connected to the end of arm tooling through tubing 14 and fitting 15. As depicted in FIG. 4, the vacuum and air sources are located in a housing on top of the robotic arm, but other locations for vacuum and air sources, either attached to or separated from the robotic assembly, are contemplated in other embodiments. Optionally, the sample sorting device includes a tube sensor 12, configured to sense whether a sample tube has been picked up and retained by the end of arm tooling when a vacuum is applied, and to convey this information to a control system.

Figure 5:
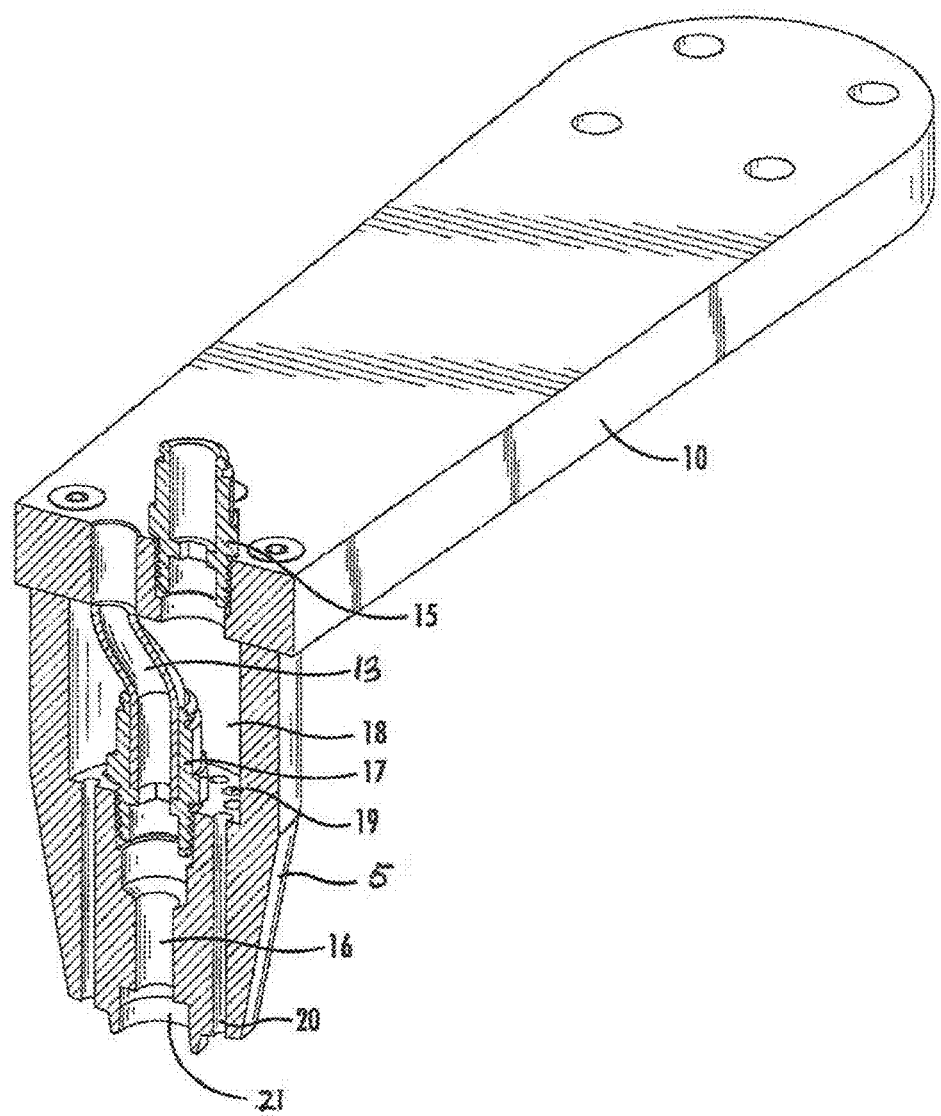
FIG. 5 shows a cross-section of an embodiment of end of arm tooling on a robotic arm of a sample tube sorting device.

FIG. 5 shows a cross-section of an embodiment of the end of arm tooling. In the embodiment depicted in FIG. 5, the end of arm tooling includes a portion of vacuum tubing 13 that extends into the interior of the tooling, and that is connected to an open column 16 in a lower portion of the tooling. Open column 16 is connected to an adaptor 21 at the bottom of the tooling that is configured to connect with and retain the top of a sample tube by suction when a vacuum is applied. The end of arm tooling also includes an open chamber 18 that is located within an upper portion of the tooling and that surrounds fitting 17. Open chamber 18 is fluidly connected to an air source via tubing (not shown) and fitting 15, through which air passes into the top of chamber 18 when air pressure is applied. Air passes through chamber 18 and through a plurality of openings 19 that extend from the bottom of chamber 18 through the lower portion of the tooling, expelling air through openings 20 at the bottom of the tooling when air pressure is applied during acquisition of a sample tube by the end of arm tooling.

Figure 6:
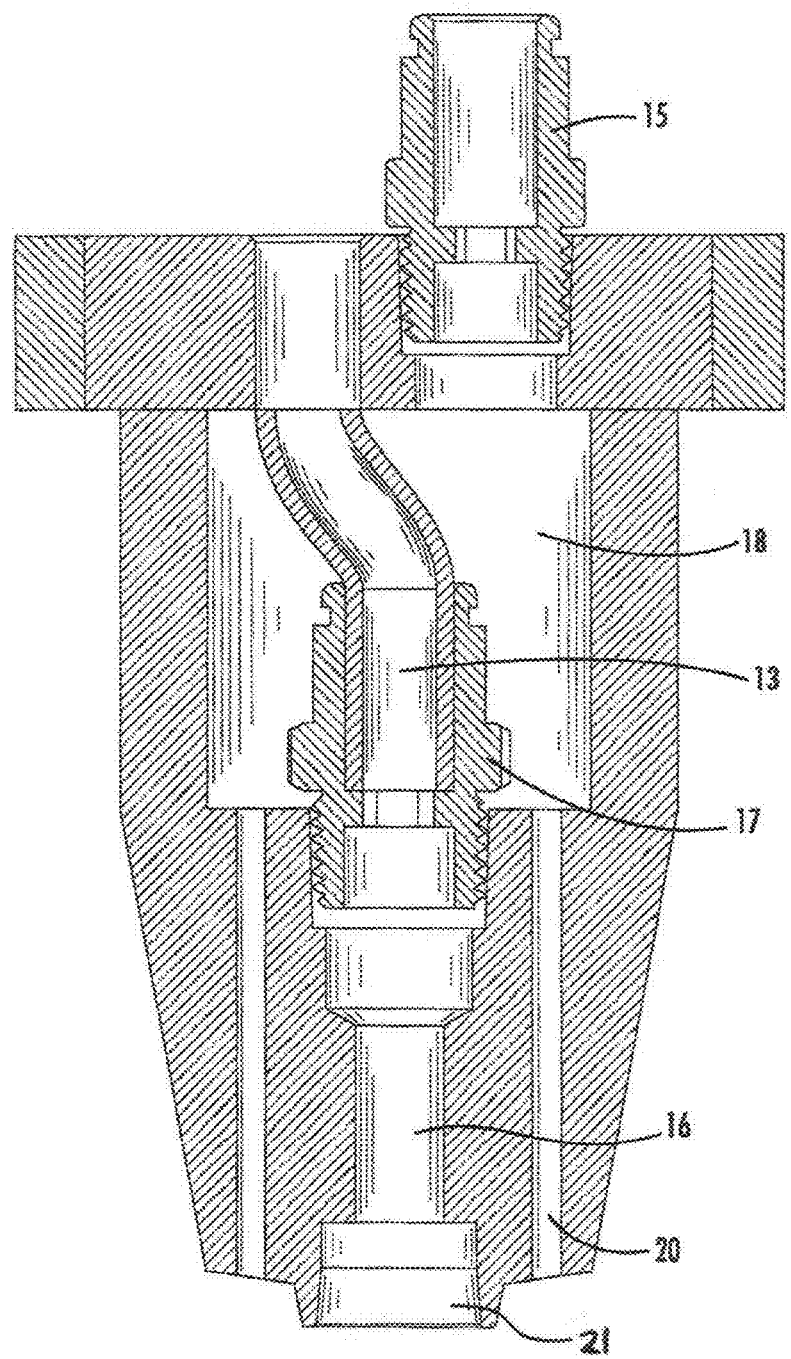
FIG. 6 shows an interior view of an embodiment of end of arm tooling on a robotic arm of a sample tube sorting device.

FIG. 6 shows an interior view of an embodiment of the end of arm tooling 5. Sample tubes are picked up and retained in adaptor 21 by vacuum and expelled in a desired location by brief application of positive air pressure through column 16 and adaptor 21. The adaptor is fluidly connected to a vacuum source via column 16, which is connected to tubing 13 via fitting 17. Tubing 16 is connected to a vacuum source. Sample tubes are expelled in a desired location when the vacuum is terminated and air is expelled briefly through the end of arm tooling.

Figure 7:
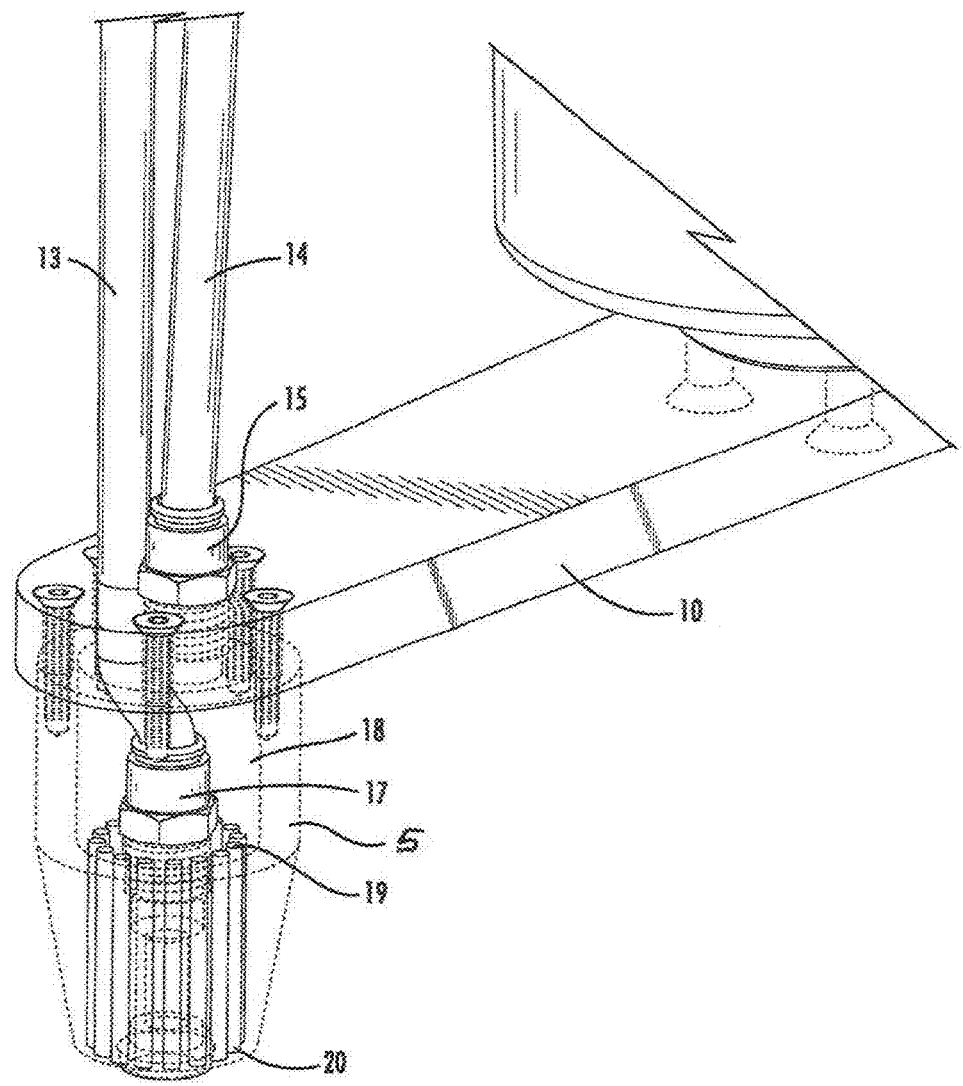
FIG. 7 shows an interior view of an embodiment of end of arm tooling on a robotic arm of a sample tube sorting device.

FIG. 7 shows an interior view of an embodiment of the end of arm tooling 5, with further detail of a ring of openings 19 that extend from the bottom of chamber 18, terminating at the bottom of the tooling in openings 20 through which air is expelled when sample tubes are acquired by the end of arm tooling, holding surrounding tubes in the sample tube rack in place and preventing interference from the surrounding tubes as the tube of interest is picked up.

Figure 8:
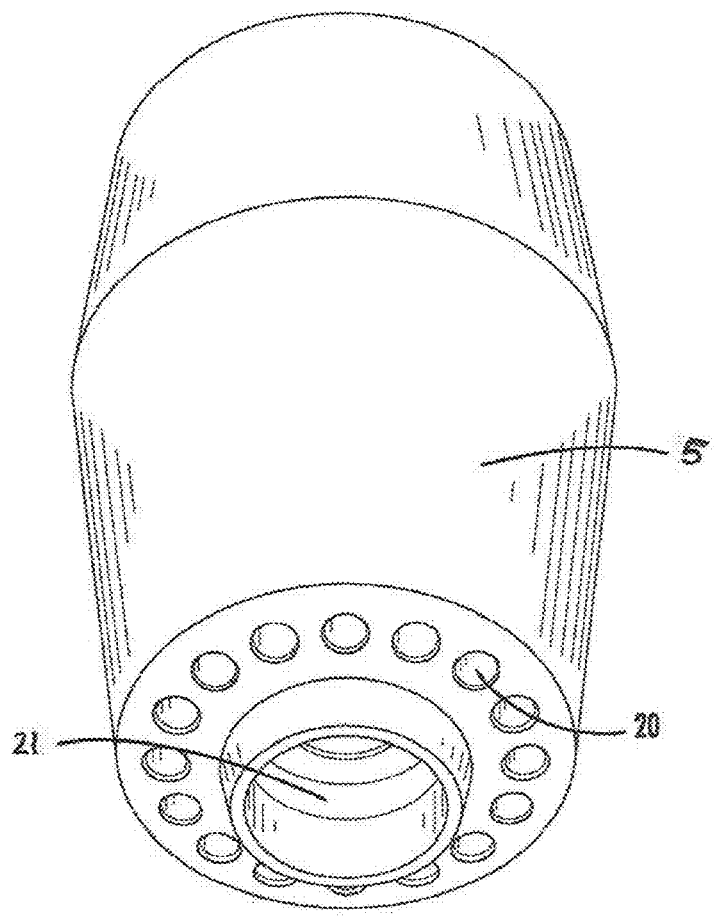
FIG. 8 shows an exterior view of an embodiment of end of arm tooling on a robotic arm of a sample tube sorting device.

FIG. 8 shows an embodiment of end of arm tooling 5, with a ring of openings 20, through which air may be expelled when positive air pressure is applied, surrounding adaptor 21, which may retain a sample tube when a vacuum is applied.

Figure 9:
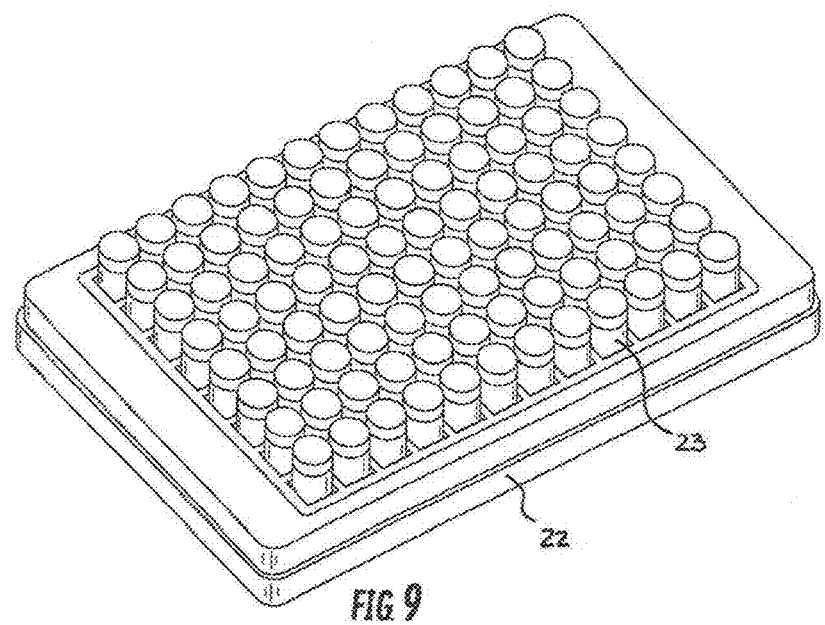
FIG. 9 shows an embodiment of a sample tube rack with sample tubes.
Figure 10:
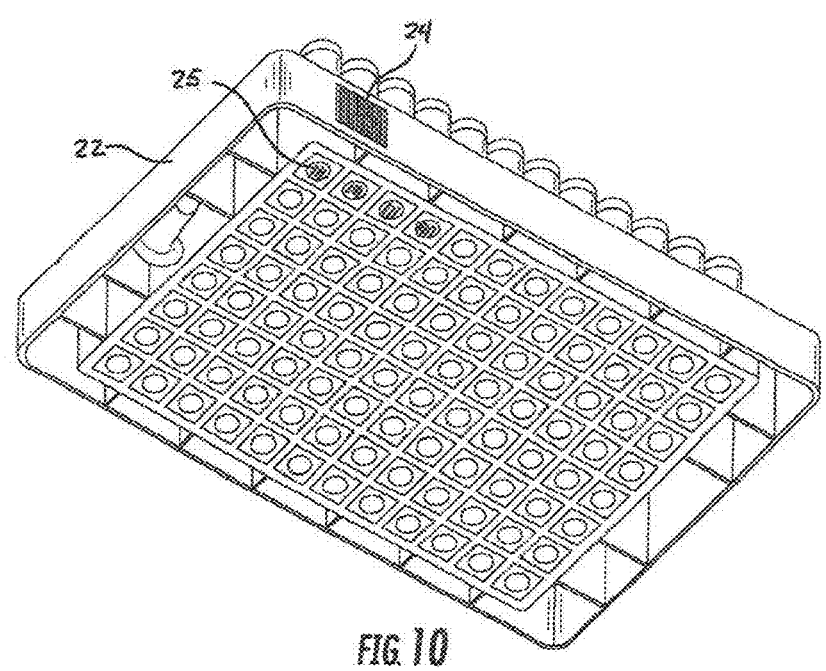
FIG. 10 shows an embodiment of a sample tube rack with coded information on one side (depicted as coded information along a length side of the sample tube rack) and sample tubes with coded information on the bottoms of tubes.
Figure 11:
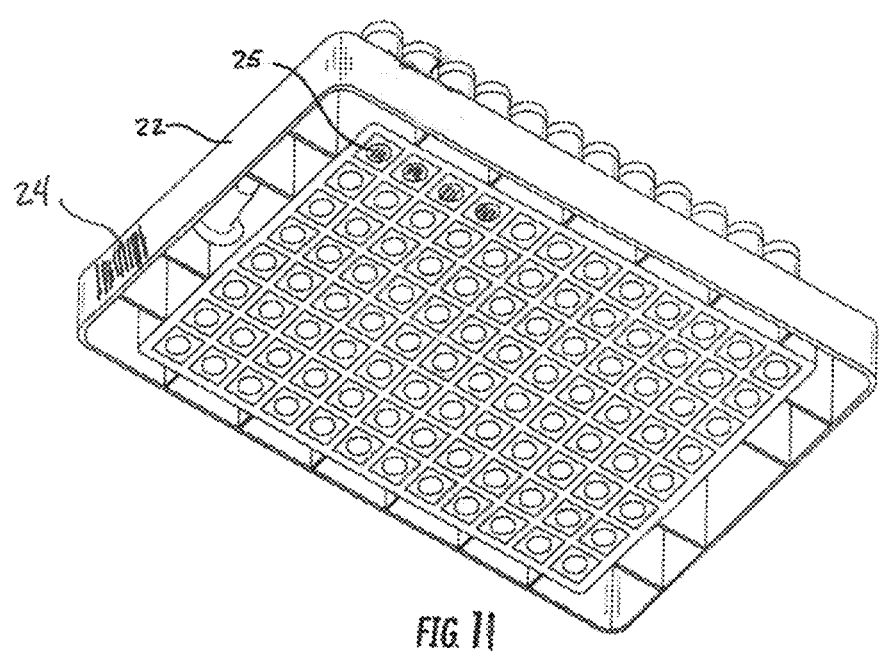
FIG. 11 shows an embodiment of a sample tube rack with coded information on one side (depicted as coded information along a width side of the sample tube rack) and sample tubes with coded information on the bottoms of tubes.

FIG. 9 shows an embodiment of a sample tube rack 22 that contains sample tubes 23. FIG. 10 shows an embodiment in which coded information is on the bottoms of sample tubes and viewable through the bottom of slots into which the tubes are inserted in the sample rack 25, and in which coded information 24 is on the length side of the sample rack. FIG. 11 shows an embodiment in which coded information is on the bottoms of sample tubes and viewable through the bottom of slots into which the tubes are inserted in the sample rack 25, and in which coded information 24 is on the width side of the sample rack. In some embodiments, coded information may be contained on both length and width sides of the sample tube rack (not depicted).

LIMS

In some embodiments, a sample tube sorting device as described herein is integrated with a laboratory information management system (LIMS), as described below.

A LIMS, also referred to as a laboratory management system (LMS) or a laboratory information system (LIS), is a system for modernizing functions within a laboratory that have traditionally been performed manually or semi-manually. A LIMS system may include but is not limited to a server or host computer, database, management software, and may be coupled to associated laboratory instrumentation for performing respective laboratory functions. A LIMS system will generally assist laboratory personnel in tracking, analyzing, sorting, and routing laboratory samples throughout complex laboratory processes in an efficient and cost-effective manner.

Advantages of LIMS systems include, but are not limited to, enhanced sample management, quality control, chain of custody, and report generation. A LIMS system also permits flexible control of access to laboratory information among a diverse user set, such as physicians, patients, analysts, and technicians.

A LIMS as disclosed herein provides for automation and laboratory information management, and may be embodied as a system, method, or computer program product. Furthermore, the present invention may take the form of an entirely software embodiment, entirely hardware embodiment, or a combination of software and hardware embodiments. Even further, the present invention may take the form of a computer program product contained on a computer-readable storage medium, where computer-readable code is embodied on the storage medium. In another embodiment, the present invention may take the form of computer software implemented as a service (SaaS). Any appropriate storage medium may be utilized, such as optical storage, magnetic storage, hard disks, or CD-ROMs.

Figure 13:
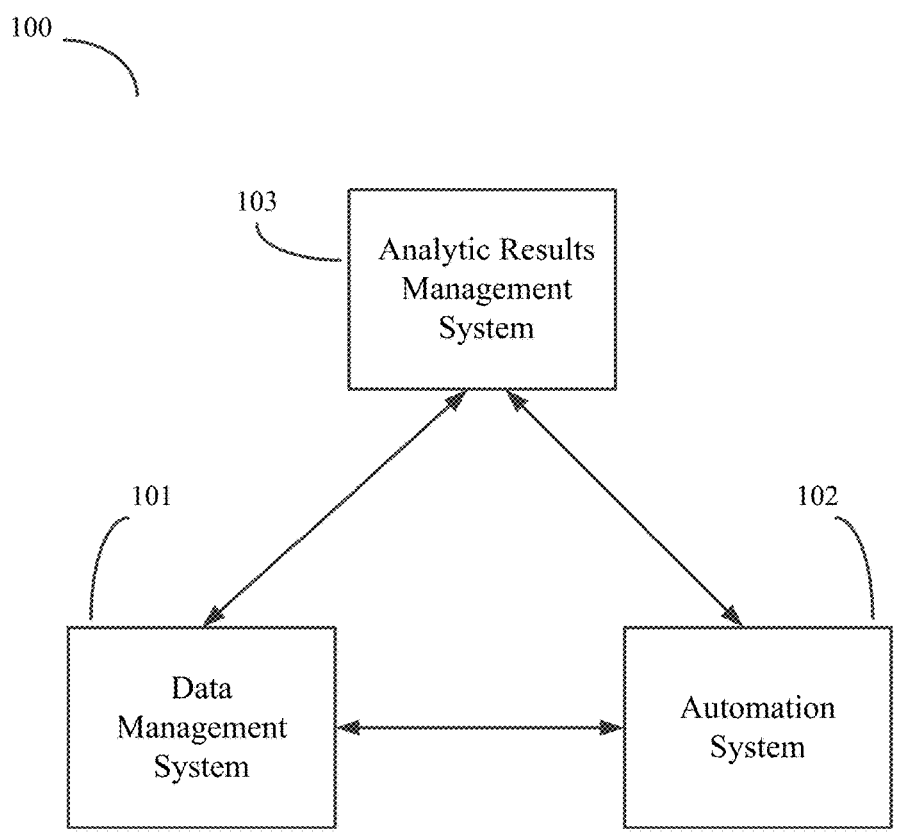
FIG. 13 illustrates an overview of an automatic diagnostic laboratory and a laboratory information management system.

FIG. 13 illustrates an overview of system 100 for an automatic diagnostic laboratory and laboratory information management system (hereinafter "LIMS"). System 100 includes a data management system 101, automation system 102, and analytics results management system (ARMS) 103. In general, data management system 101 is a centralized database tool for maintaining information pertaining to the LIMS system, such as maintaining laboratory tests, diagnostics, equipment, personnel, and the like. In one embodiment, data management system 101 is dynamically updated and facilitates the management of information among other components of the LIMS system, such as automation system 102 and ARMS 103.

Automation system 102 generally provides for the management of laboratory workflow, and may permit one or more users to create and deploy custom laboratory workflow processes. For example, automation system 102 may provide functionality for a user to create a graphical diagram to model different laboratory equipment and diagnostics, and may permit the user to customize the timing, decision-making, and other test variables of laboratory analytics. Automation system 102 may further provide functionality to permit a user to deploy one or more workflow processes based on user-generated diagrams, and such workflow processes may be modified dynamically by the user. Furthermore, automation system 102 may include hardware and software components for interfacing with laboratory equipment, such as robotics units, conveyor systems, sample repositories, climate control systems, (e.g., lighting and temperature), pneumatic systems, audio/video systems, etc.

In one embodiment, automation system 102 may include hardware and/or software for enabling one or more robotics units to perform movements related to testing laboratory samples, such as mixing, shaking, heating, cooling, picking, and/or placing or samples. For example, automation system 102 may generate and send commands to the one or more robotics units to allow the robotics units to move in three-dimensional space. Such commands may also permit the one or more robotics units to interface with a pneumatics system to utilize pressurized air for grasping and releasing one or more samples. In one embodiment, the samples may be contained in a test tube, vial, or similar container. Automation system 102 may further be configured to generate and send commands to the one or more robotics units to allow the robotics units to remove and/or replace a lid on the top of a container. For example, the one or more robotics units may be equipped with machinery capable of sensing a test tube lid, and further capable of removing the test tube lid by one or more robotic motions. Similarly, the one or more robotics units may be equipped with machinery to sense a test tube without a lid, and may perform one or more robotic motions to place and seal the test tube with a lid, for example.

ARMS 103 generally provides a system for dynamically rendering and organizing laboratory information, including but not limited to information such as diagnostic results, quality control metrics, historical test data, sample genotypes, and the like. For example, ARMS 103 may facilitate the generation of interactive data visualizations to permit one or more users to effectively oversee laboratory chemistry, algorithms, and products. ARMS 103 may also permit one or more users to perform complex analytical functions, such as analyze and manipulate quality control constraints, synthesize raw test data, and manually correct test results.

In one embodiment, one or more components of the data management system 101, automation system 102, and/or ARMS 103 may be maintained at a location local to the laboratory and associated equipment (e.g., a server room). In another embodiment, one or more components of the data management system 101, automation system 102, and/or ARMS 103 may be maintained at a location remote from the laboratory and associated equipment (e.g., a "cloud-based" system). In yet another embodiment, one or more components of the data management system 101, automation system 102, and/or ARMS 103 may be maintained in a combination of local and remote locations.

Figure 14:
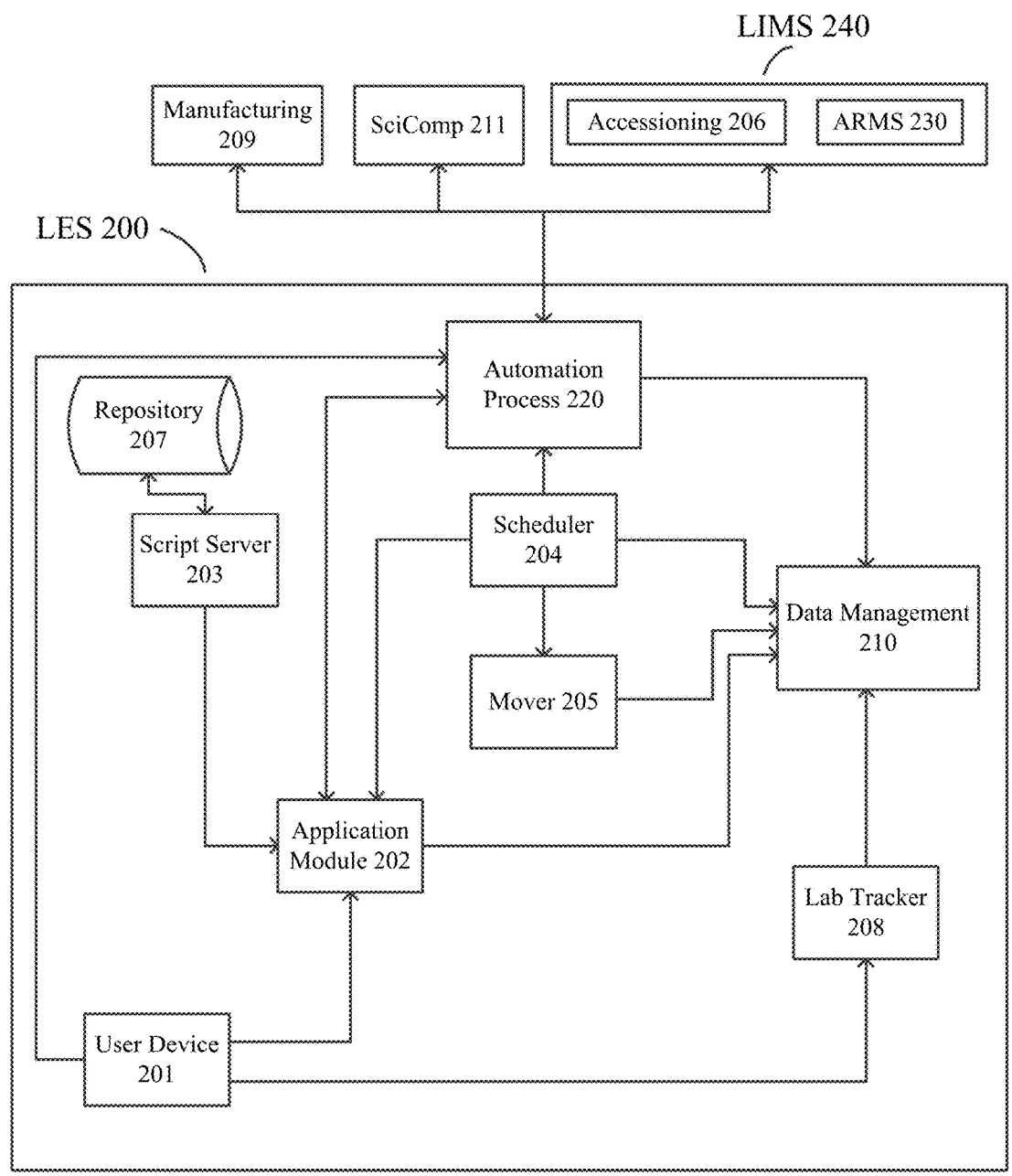
FIG. 14 illustrates a detailed view of a laboratory execution system for facilitating laboratory automation.

FIG. 14 illustrates a detailed view of a laboratory execution system (LES) 200. LES 200 may include a data management tool 210 and an automation process 220. Furthermore, LES 200 may communicate with a LIMS module 240. In one embodiment, LIMS module 240 may include at least an accessioning module 206 and an analytic results management system (ARMS) 230, which are discussed in more detail with respect to FIG. 15. FIG. 14 further depicts user device 201 and application module 202, which will now be described. User device 201 may permit a user to interact with LES 200 and thus facilitate user interaction with each of the data management tool 210, automation process 220, and ARMS 230, and/or other associated systems. User device 201 may communicate with application module 202 in order to perform one or more functions as described herein.

In one embodiment, application module 202 may be an application programming interface (API) for performing one or more automated functions. In another embodiment, application module 202 may be a graphical user interface (GUI), whereby a user may instruct LES 200 to perform one or functions such as loading a script, running a diagnostic method, executing a laboratory instrument action, or the like. User device 201 may also interface with LES 200 by direct interaction with other components of the system. For example, user 201 may provide a command directly to scheduler 204 for fixing execution time errors.

In another embodiment, lab tracker 208 facilitates physical location management of one or more robotics units. For example, lab tracker 208 may be configured as a database which stores positional information of all physical objects for a given point in time. Lab tracker 208 may also receive information from other components in LES 200. For example, user 201 may provide a command to lab tracker module 208 for fixing a plate tracking error.

FIG. 14 further depicts automation process 220, which may provide workflow management of sample plates, samples, and associated data. For example, automation process 220 may provide information regarding available plates to application module 202, or may otherwise indicate the availability of system resources to application module 202. As another example, automation process 220 may receive reporting information, such as a job completion report, from application module 202. Automation process 220 may also receive seed pipeline information, which may be manually entered by a user and provided directly to the automation process 220 from user device 201. Seed pipeline information may include, for example, information to instantiate new objects for management into the LIMS system. For example, a user may utilize a GUI in order to create research samples, where the research samples are introduced as seed pipeline information into automation process 220.

In another embodiment, automation process 220 may receive seed pipeline information from an accessioning module 206. In yet another embodiment, automation process 220 may receive query information from ARMS 230, for example, a query regarding results to be displayed. Automation process 220 may further receive query information from scheduler 204, for example, a query regarding a pending job. Furthermore, automation process 220 may provide data management tool 210 with data validation information and information regarding data queries.

Furthermore, FIG. 14 shows data management tool 210, which will now be described. Data management tool 210 may be configured to integrate quantitative data, track sample barcodes, and manage overall workflow of LES 200. In one embodiment, data management tool 210 may receive information regarding a report operation from application module 202. In another embodiment, data management tool 210 may receive a report operation from mover module 205. Furthermore, data management tool 210 may receive a command to fix plate tracking errors from a user via lab tracker module 207. In yet another embodiment, data management tool 210 may receive, from scheduler 204, a query regarding stateful data. In one example, such a query pertains to seal, spin, or location information.

FIG. 14 further depicts script server 203 and repository 207, which will now be described. In one embodiment, script server 203 may communicate with a version control system (VCS) repository 207 in order to obtain one or more software scripts for use in operating LES 200. VCS repository 207 may be maintained by known repositories such as "Github," or any other appropriate VCS repository service, as will be appreciated by one of ordinary skill in the art. In one embodiment, script server 203 may obtain software scripts from VCS repository 207, and may further push one or more software scripts to application module 202. Script server 203 may be further configured to deploy scripts and manage script metadata.

Scheduler 204 may be configured to automate scheduling and execute applications. For example, scheduler 204 may include at least one software module such as script compiler, scheduler, and/or executor. In one embodiment, scheduler 204 may provide application module 202 with one or more commands for performing an action, or may further provide application module 202 with a query for an API function. In another embodiment, scheduler 204 may be configured to initiate and/or deliver one or more queries for an API function, and may be further configured to initiate and/or deliver one or more queries regarding stateful data. In another embodiment, scheduler 204 may be configured to initiate and/or deliver one or more queries regarding a pending job. In yet another embodiment, scheduler 204 may be configured to receive a command to fix execution time errors.

Mover application 205 may be configured to communicate with one or more robotics units within a laboratory environment. For example, mover application 205 may facilitate the directing of the one or more robotics units to perform one or more movements in three-dimensional space. Mover application 205 may send instructions to the one or more robotics units regarding a movement, path, direction, or other information relating to three-dimensional space in which the one or more robotics units may perform any number of movements. In another embodiment, scheduler 204 may provide mover module 205 with one or more commands for performing a move, such as, for example, robotic movements described in detail with respect to FIG. 18.

Additionally, LES 200 may be configured to communicate with manufacturing module 209. In one embodiment, manufacturing module 209 is configured to provide LES 200 with information related to sample components, such as plastic, reagents, and the like. For example, manufacturing module 209 may assist in identifying sample components which are introduced into LES 200. In another embodiment, manufacturing module 209 may be configured to declare and generate barcode labels for one or more sample plates and sample tubes.

LES 200 may further communicate with SciComp module 211. In one embodiment, SciComp module 211 may facilitate overall automation within the LIMS system by managing the processing of all main stages, including but not limited to (i) physical sample acquisition, (ii) sequencing, (iii) raw data generation, (iv) data analysis, and (v) transfer of analyzed data to ARMS. In one example, SciComp module 211 may assist automation process 220 by querying automation process 200 for information pertaining to a next job to process. SciComp module 211 may further include components such a script server and/or scheduler for maintaining efficient job workflow. In one embodiment, SciComp module 211 may perform the necessary data analytics tasks of the LIMS system, and may run the necessary algorithms to automatically produce patient variant calls from raw data to analyzed data.

Although only one instance of each module is listed on FIG. 14 (e.g. one scheduler 204 and one mover 205), LES 200 may include one or more instances of any such module. For example, there may be two or more instances of scheduler 204, which are each associated with a specific process or device within the laboratory environment.

Figure 15:
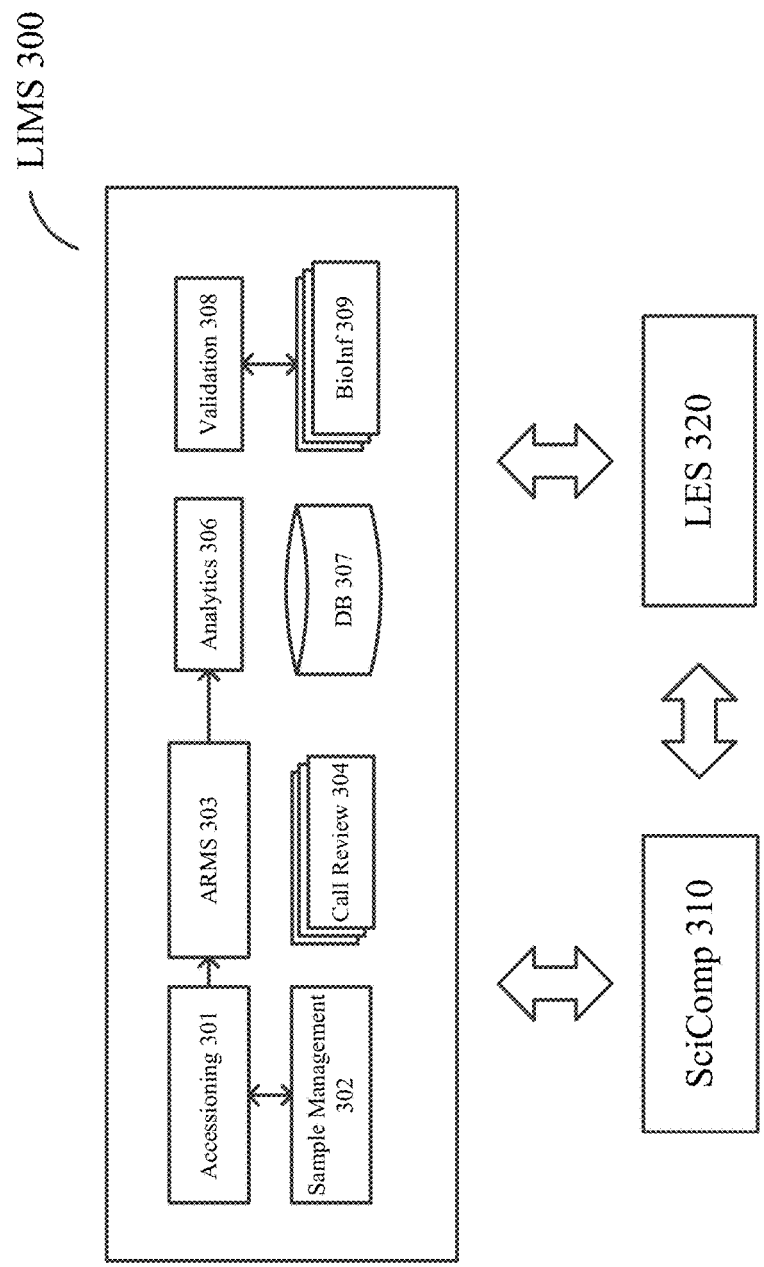
FIG. 15 illustrates a detailed view of a laboratory information management system for facilitating laboratory automation.

FIG. 15 illustrates a detailed depiction of laboratory information management system (LIMS) 300. In one embodiment, LIMS 300 includes an accessioning module 301 and sample management module 302. Accessioning module 301 may be configured to record the arrival of a sample and instantiate the arrival of the sample within one or more databases. For example, accessioning module 301 may be configured to send a first set of information to ARMS 303. The first set of information may include, for example, information pertaining to a disease panel order. Sample management module 302 may be configured to communicate with accessioning module 301 in the organization of one or more samples to be seeded to ARMS 303. Analytics module 306 may receive one or more outputs from ARMS 303, such as results pertaining to a disease panel order. LIMS 300 may further include validation module 308 and bioinformation module 309. Validation module 308 and bioinformation module 309 may each be configured to assist in the development of sample assays for testing.

As depicted in FIG. 15, LIMS 300 may further communicate with LES 310 and SciComp 320, as discussed with respect to FIG. 14. LIMS 300 may further include a call review module 304, which may be configured to provide processing techniques to review and modify variant call processing data. LIMS 300 may further include a database module 307 to store information relating to samples and associated test data, as used within LIMS 300.

ARMS 303 may be further configured as a database containing genotypes for samples. For example, ARMS 303 may be configured to process, maintain, and deliver information regarding genotyping data based on one or more Variant Call Format (VCF) files. As will be appreciated by one of ordinary skill in the art, a VCF file is a standardized text file format for representing and storing gene sequence variations. In one embodiment, ARMS 303 may provide a results query to an automation process on LES 320. For example, a results query may be utilized to determine which results are capable of being displayed.

In another embodiment, ARMS 303 includes functionality for generating a GUI, where the GUI provides a user with real-time data corresponding to laboratory diagnostics and analysis for one or more samples. The GUI may permit the user to perform a plurality of functions, including but not limited to quality control (QC) monitoring and adjustment, sample history generation, manual tagging of samples, and the ability to manually pass or fail a given sample. ARMS 303 may include functionality for generating custom diagnostics reports, including the generation of graphs, tables, spreadsheets, plots, diagrams, and/or other visualization to enable efficient data interpretation.

Figure 16:
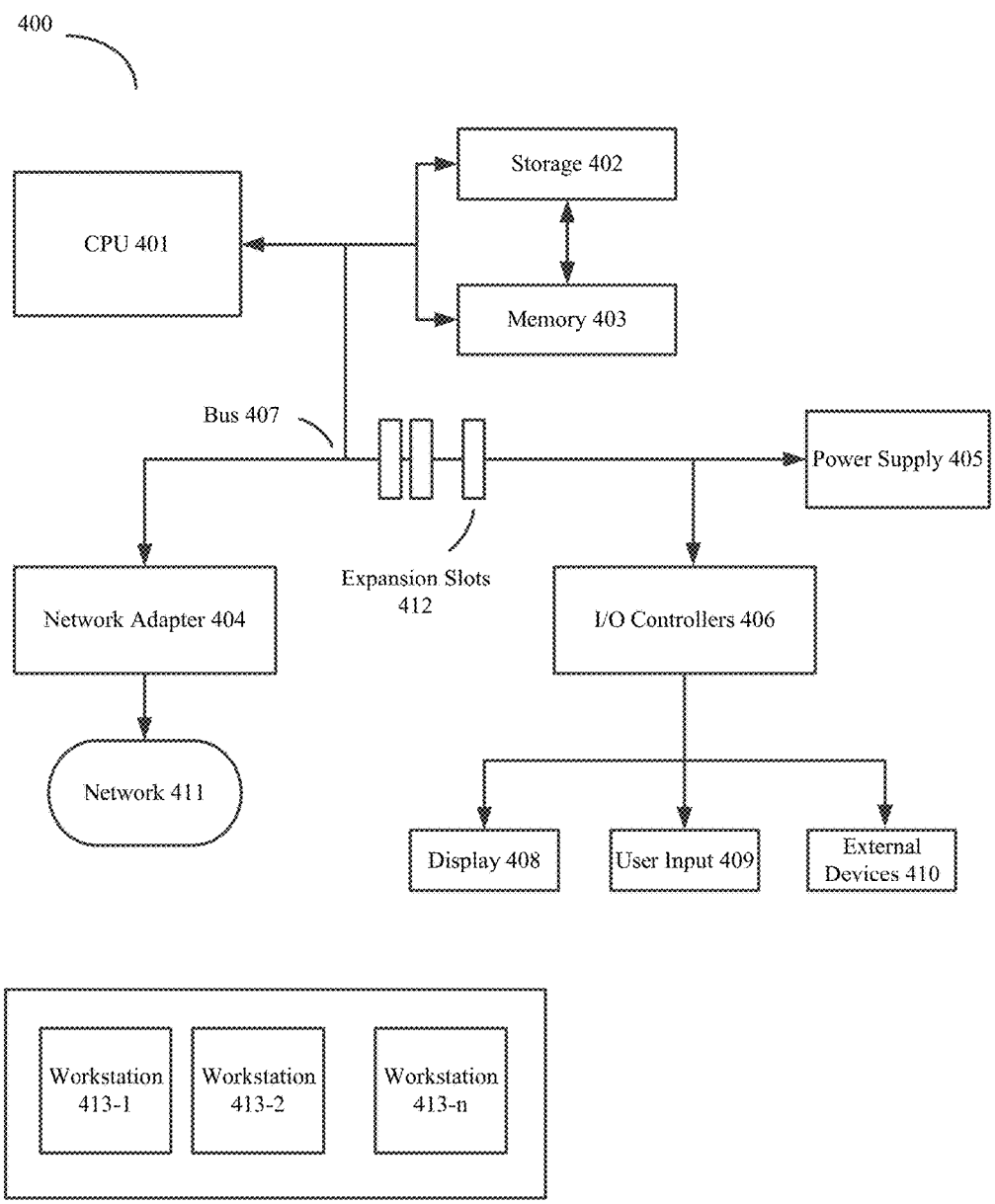
FIG. 16 illustrates a general computing system in which one or more systems may be implemented.

FIG. 16 illustrates a general purpose computing system 400 in which one or more systems, as described herein, may be implemented. System 400 may include, but is not limited to known components such as central processing unit (CPU) 401, storage 402, memory 403, network adapter 404, power supply 405, input/output (I/O) controllers 406, electrical bus 407, one or more displays 408, one or more user input devices 409, and other external devices 410. It will be understood by those skilled in the art that system 400 may contain other well-known components which may be added, for example, via expansion slots 412, or by any other method known to those skilled in the art. Such components may include, but are not limited to, hardware redundancy components (e.g., dual power supplies or data backup units), cooling components (e.g., fans or water-based cooling systems), additional memory and processing hardware, and the like.

System 400 may be, for example, in the form of a client-server computer capable of connecting to and/or facilitating the operation of a plurality of workstations or similar computer systems over a network. In another embodiment, system 400 may connect to one or more workstations over an intranet or internet network, and thus facilitate communication with a larger number of workstations or similar computer systems. Even further, system 400 may include, for example, a main workstation or main general purpose computer to permit a user to interact directly with a central server. Alternatively, the user may interact with system 400 via one or more remote or local workstations 413. As will be appreciated by one of ordinary skill in the art, there may be any practical number of remote workstations for communicating with system 400.

CPU 401 may include one or more processors, for example Intel® Core™ i7 processors, AMD FX™ Series processors, or other processors as will be understood by those skilled in the art. CPU 401 may further communicate with an operating system, such as Windows NT® operating system by Microsoft Corporation, Linux operating system, or a Unix-like operating system. However, one of ordinary skill in the art will appreciate that similar operating systems may also be utilized. Storage 402 may include one or more types of storage, as is known to one of ordinary skill in the art, such as a hard disk drive (HDD), solid state drive (SSD), hybrid drives, and the like. In one example, storage 402 is utilized to persistently retain data for long-term storage. Memory 403 may include one or more types memory as is known to one of ordinary skill in the art, such as random access memory (RAM), read-only memory (ROM), hard disk or tape, optical memory, or removable hard disk drive. Memory 403 may be utilized for short-term memory access, such as, for example, loading software applications or handling temporary system processes.

As will be appreciated by one of ordinary skill in the art, storage 402 and/or memory 403 may store one or more computer software programs. Such computer software programs may include logic, code, and/or other instructions to enable processor 401 to perform the tasks, operations, and other functions as described herein, and additional tasks and functions as would be appreciated by one of ordinary skill in the art. Operating system 402 may further function in cooperation with firmware, as is well known in the art, to enable processor 401 to coordinate and execute various functions and computer software programs as described herein. Such firmware may reside within storage 402 and/or memory 403.

Moreover, I/O controllers 406 may include one or more devices for receiving, transmitting, processing, and/or interpreting information from an external source, as is known by one of ordinary skill in the art. In one embodiment, I/Ocontrollers 406 may include functionality to facilitate connection to one or more user devices 409, such as one or more keyboards, mice, microphones, trackpads, touchpads, or the like. For example, I/O controllers 406 may include a serial bus controller, universal serial bus (USB) controller, FireWire controller, and the like, for connection to any appropriate user device. I/O controllers 406 may also permit communication with one or more wireless devices via technology such as, for example, near-field communication (NFC) or Bluetooth™. In one embodiment, I/O controllers 406 may include circuitry or other functionality for connection to other external devices 410 such as modem cards, network interface cards, sound cards, printing devices, external display devices, or the like. Furthermore, I/O controllers 406 may include controllers for a variety of display devices 408 known to those of ordinary skill in the art. Such display devices may convey information visually to a user or users in the form of pixels, and such pixels may be logically arranged on a display device in order to permit a user to perceive information rendered on the display device. Such display devices may be in the form of a touch-screen device, traditional non-touch screen display device, or any other form of display device as will be appreciated be one of ordinary skill in the art.

Furthermore, CPU 401 may further communicate with I/O controllers 406 for rendering a graphical user interface (GUI) on, for example, one or more display devices 408. In one example, CPU 401 may access storage 402 and/or memory 403 to execute one or more software programs and/or components to allow a user to interact with the system as described herein. In one embodiment, a GUI as described herein includes one or more icons or other graphical elements with which a user may interact and perform various functions. For example, GUI 407 may be displayed on a touch screen display device 408, whereby the user interacts with the GUI via the touch screen by physically contacting the screen with, for example, the user's fingers. As another example, GUI may be displayed on a traditional non-touch display, whereby the user interacts with the GUI via keyboard, mouse, and other conventional I/O components 409. GUI may reside in storage 402 and/or memory 403, at least in part as a set of software instructions, as will be appreciated by one of ordinary skill in the art. Moreover, the GUI is not limited to the methods of interaction as described above, as one of ordinary skill in the art may appreciate any variety of means for interacting with a GUI, such as voice-based or other disability-based methods of interaction with a computing system.

Moreover, network adapter 404 may permit device 400 to communicate with network 411. Network adapter 404 may be a network interface controller, such as a network adapter, network interface card, LAN adapter, or the like. As will be appreciated by one of ordinary skill in the art, network adapter 404 may permit communication with one or more networks 411, such as, for example, a local area network (LAN), metropolitan area network (MAN), wide area network (WAN), cloud network (IAN), or the Internet.

One or more workstations 413 may include, for example, known components such as a CPU, storage, memory, network adapter, power supply, I/O controllers, electrical bus, one or more displays, one or more user input devices, and other external devices. Such components may be the same, similar, or comparable to those described with respect to system 400 above. It will be understood by those skilled in the art that one or more workstations 413 may contain other well-known components, including but not limited to hardware redundancy components, cooling components, additional memory/processing hardware, and the like.

Figure 17:
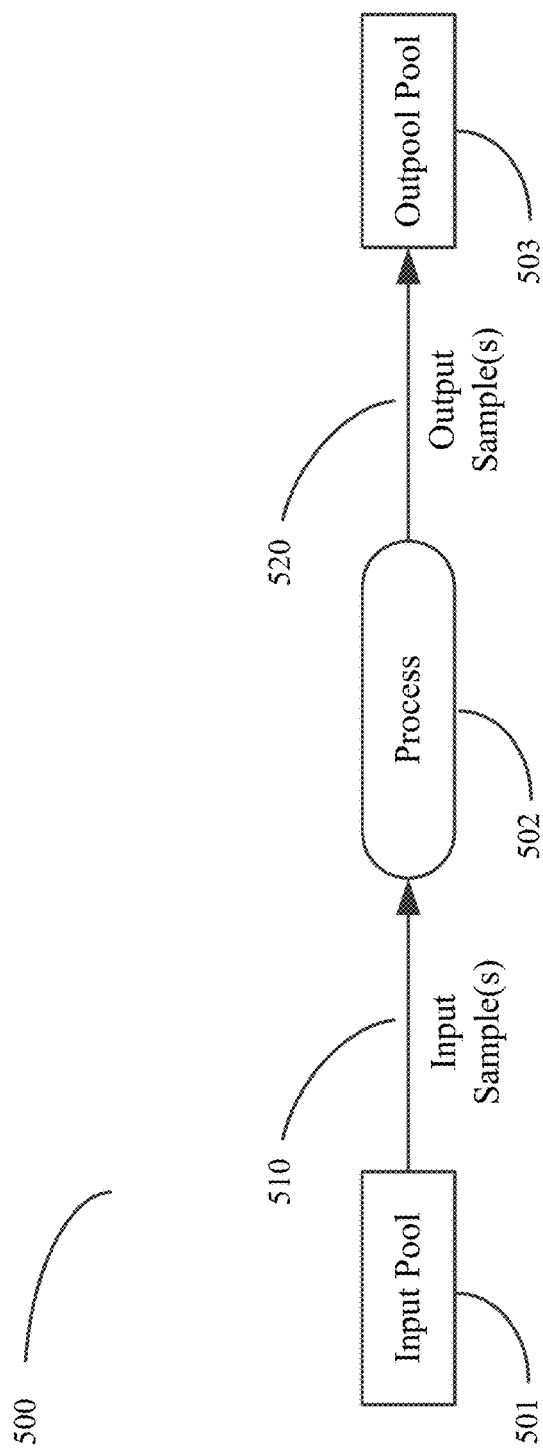
FIG. 17 illustrates an exemplary workflow diagram for sample processing.

FIG. 17 illustrates an exemplary laboratory process 500 facilitated by, for example, automation process 220 in FIG. 14. In one embodiment, automation process 220 provides a user with the ability to create lab workflow processes in order to maintain sample queues for diagnostics and analysis. For example, a user may create one or more graphical objects on a GUI display, where the objects may represent one or more laboratory states, decisions, inputs, outputs, or other conditions to model a laboratory process. A resulting laboratory process may be created based on the one or more graphical objects created by the user, such as, for example, a process as depicted in FIG. 17.

In one embodiment, process 500 includes input pool object 501, which may represent, for example, one or more polymerase chain reaction (PCR) plates. Samples from the input pool may be scheduled to undergo one or more tests, diagnostics, or other laboratory processes 502. For example, samples within the one or more PCR plates may undergo a process for DNA amplification. Arrow 510 may represent the transfer of one PCR plate 501 to amplification process 502, for example. Arrow 520 may represent a successful output of amplification process 502, such as, for example, one amplified PCR plate. Output pool 503 may represent, for example, one or more amplified PCR plates. Arrow 520 may therefore represent the transfer of one amplified PCR plate to output pool object 503. Although only one input, one process, and one output are depicted in process 500, it will be appreciated that any number of inputs, outputs, processes, transfers, or other laboratory functions may be represented by such a graphical diagram, and that the invention is not limited to the exemplary process depicted in FIG. 17.

Figure 18:
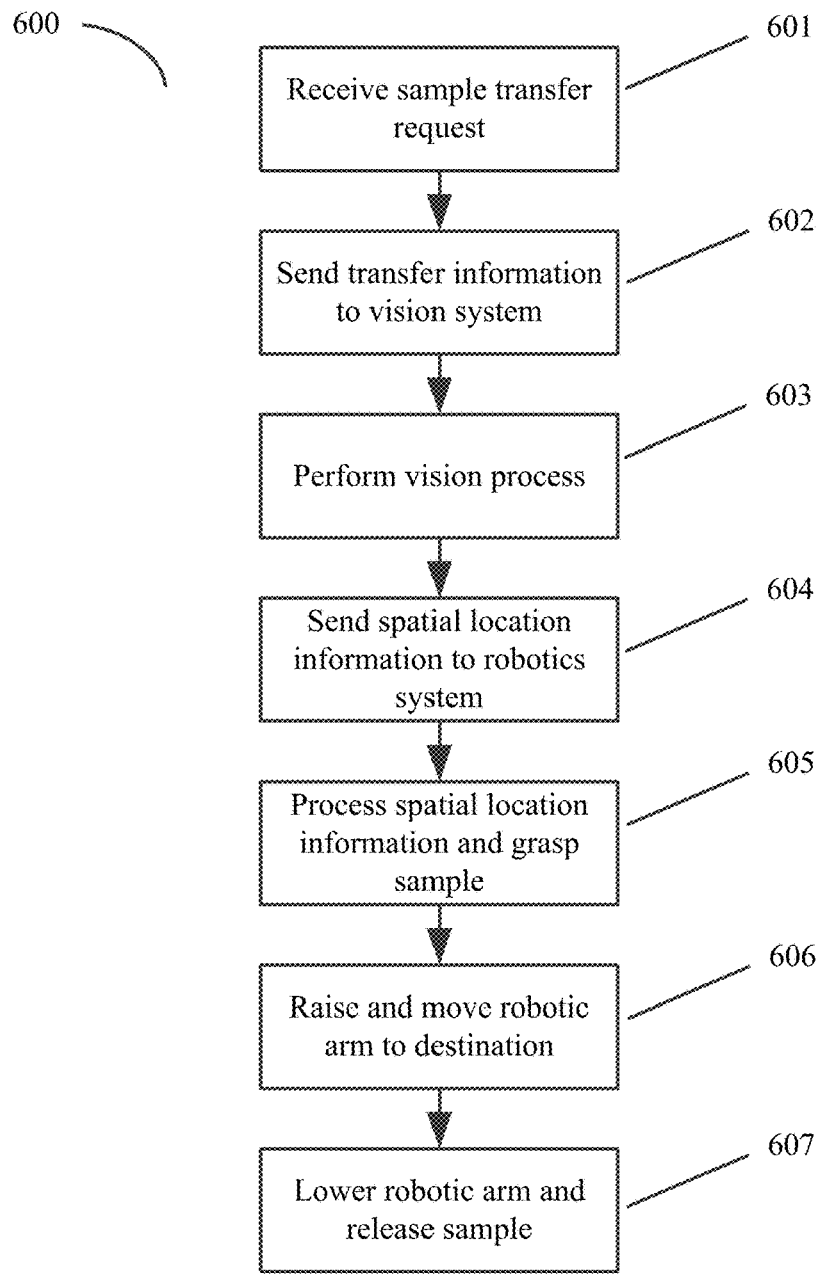
FIG. 18 illustrates an exemplary process for controlling a robotics unit to transport one or more sample tubes.

FIG. 18 illustrates an exemplary transfer process 600 for controlling a robotics unit to transport one or more sample tubes. Transfer process 600 may be facilitated at least in part by automation process 220 as described in FIGS. 13 and 14. For example, automation process 220 may communicate with hardware and software processes associated with one or more robotics, vision, and/or pneumatic systems in order to perform transfer process 600. In one embodiment, transfer process 600 is utilized to transfer at least one sample from an origin location to a destination location by using at least one robotics unit coupled with vision and pneumatics systems.

Transfer process 600 may begin at step 601, where automation process may receive a sample transfer request.

Such request may be, for example, a manual request entered by a user, or may be an automated request initiated by a pre-scheduled workflow process. In one embodiment, the request includes information identifying at least one sample barcode corresponding to a current sample, and may further include information identifying a destination location for transferring the sample associated with the sample barcode from an origin location to the destination location.

At step 602, automation process may send transfer information to a vision system in order to identify the spatial location of the identified sample. In one embodiment, the vision system performs a vision matching process at step 603 to identify if a matching barcode exists within the vision system's viewing area. If a matching barcode is found, the vision system may send corresponding spatial location information to robotics system at step 604. Such spatial location information may correspond to sample location information discovered by the vision system when identifying matching barcode in step 603. The spatial location information may be in a form readable by robotics unit in order to permit the robotics unit to identify a three dimensional location in space corresponding to the physical sample identified.

At step 605, the robotics unit may receive and process the spatial location information, and may further grasp the identified sample. For example, the robotics unit may utilize the spatial location information to move a robotic arm to a location corresponding to a position directly above the identified sample. The robotic arm may then be lowered to a location near the sample, and the arm may grasp the sample by utilizing, for example, a pneumatic system. In one example, the sample is contained in a test tube which is grasped by a robotic arm, where a pneumatic system generates a vacuum in order to grip the test tube.

At step 606, the robotic arm may be raised while grasping the sample, and the robotic arm may be moved to a location corresponding to a destination location as received in the sample transfer request. At step 607, the robotic arm may lower the sample onto a location corresponding to the desired location, and may release the sample from the robotic grip by performing one or more pneumatic processes via the pneumatic system. For example, the pneumatic system may release the grip on the sample by discharging the vacuum and briefly expelling air near the sample.

Figure 19:
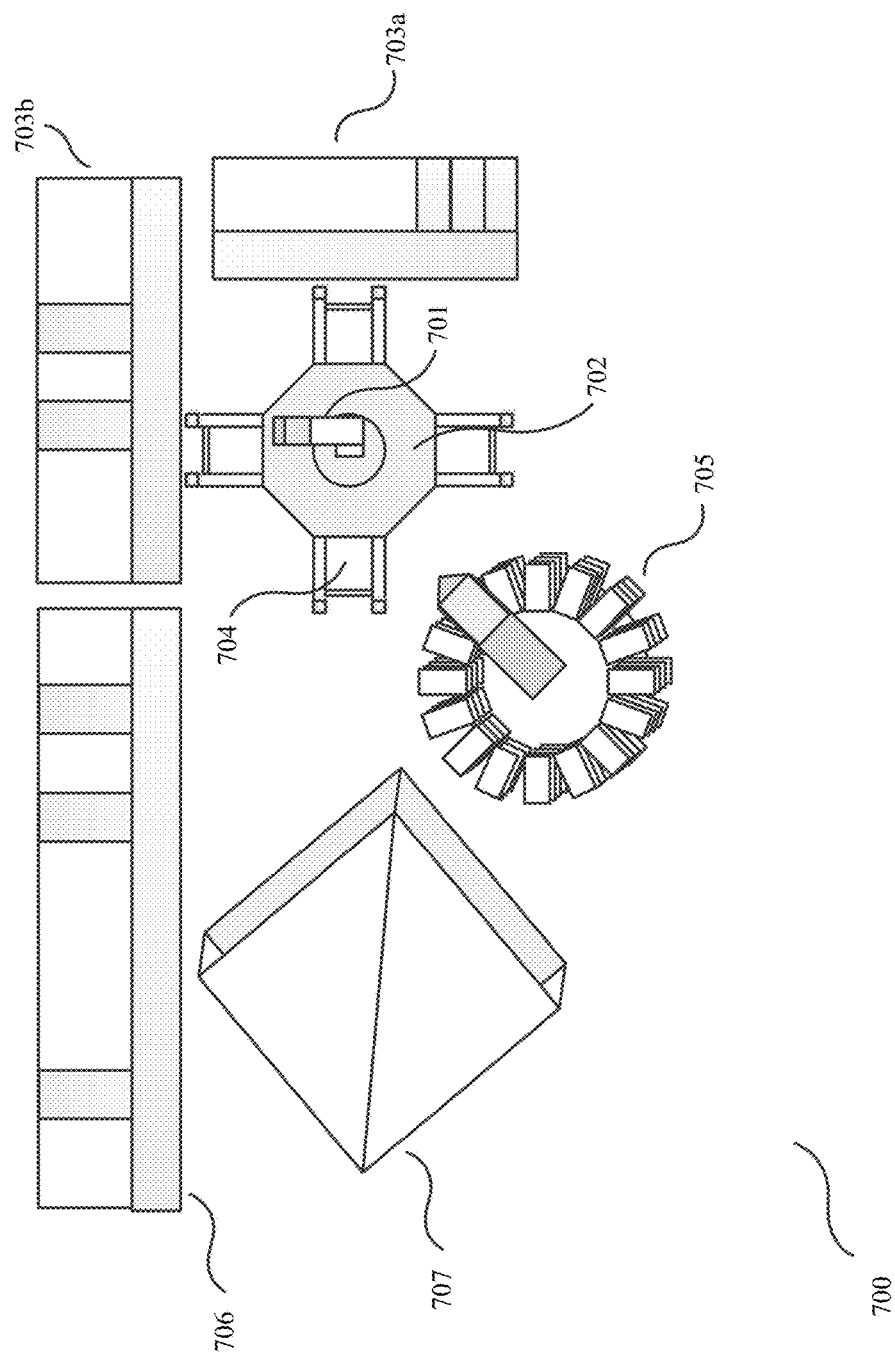
FIG. 19 illustrates a robotic system for managing automatic laboratory processes.

FIG. 19 illustrates a robotic system 700 for managing automatic laboratory processes. In one embodiment, robotic system 700 includes a robotic arm 701 for facilitating the movement of one or more samples. For example, robotic arm 701 may be configured to grasp a test tube containing a sample, and transport the test tube from a first location to a second location. In another example, robotic arm 701 may be configured to grasp a sample rack, and transport the sample rack from a first location to a second location. A sample rack may contain one or more samples, and may be stored, for example, in a sample rack repository 705. In one embodiment, sample rack repository 705 may contain one or more sample racks and may facilitate efficient storage and retrieval of one or more sample racks.

In one embodiment, robotic arm 701 may further be affixed to a robotic arm base 702, and may be configured to rotate in a 360 degree motion about the laboratory environment. For example, robotic arm 701 may extend from a first position, such as the position depicted in FIG. 19, to a second position, such as a position extending into a first liquid handling apparatus 703a. Furthermore, robotic arm 701 may, for example, retract from the extended position in first liquid handling apparatus 703a and return to the position as depicted in FIG. 19. Furthermore, robotic arm 701 may retract from the position in first liquid handling apparatus 703a, and then extend to a position within a second liquid handling apparatus 703b. In one embodiment, the robotic arm may perform various movements within liquid handling apparatus 703a and liquid handling apparatus 703b in order to facilitate various sample test procedures.

In another embodiment, robotic arm 701 may be configured to transport one or more samples and/or sample racks from sample rack repository 705 to liquid handling apparatus 703a or liquid handling apparatus 703b. Robotic arm 701 may further be configured to return one or more samples and/or sample racks from liquid handling apparatus 703a or liquid handling apparatus 703b to sample rack repository 705, for example. Furthermore, although only two liquid handling apparatus 703a and 703b are depicted in FIG. 19, one will appreciate that additional liquid handling apparatus may be deployed within the laboratory environment, and that robotic arm 701 may extend into other such areas within the reach of robotic arm 701.

In yet another embodiment, robotic arm 701 may be surrounded by one or more sensors 704. Sensors 704 may, for example, detect specific motions within an area surrounding robotic arm 701, such as a predefined motion detection area. In one embodiment, the motion detection area may be defined by a spherical or semi-spherical region centered at or near a coupling point of robotic arm 701 to robotic arm base 702. In another embodiment, the motion detection area may be defined by a spherical or semi-spherical region centered at or near a specific point in space defined by a user. For example, the motion detection area may be dynamically configured and updated by a user, and may define custom three-dimensional areas in space surrounding robotic arm 701.

Sensors 704 may, for example, provide signals to one or more software systems within the laboratory environment in order to prevent robotic arm 701 from moving into specific areas within the laboratory environment. In one example, sensors 704 may be configured to detect movements associated with a user or other object within a specified motion detection area near robotic arm 701. If sensors 704 detect such motions, sensors 704 may send one or more alarm signals to software systems associated with robotic arm 701 in order to cease all movements of robotic arm 701. Sensors 704 may be configured to, for example, send signals to software systems associated with robotic arm 701 in order to resume movements of robotic 701 upon the sensors 704 detecting that any such user, object, or other event causing the alarm signals is no longer within the motion detection area. In another embodiment, sensors 704 and robotic arm 701 may remain disabled after the alarm signal until a predefined user restart process is initiated and completed. Upon completion of such user restart process, the robotic arm 701 and sensors 704 may, for example, resume normal operations.

In another embodiment, robotic system 700 includes an additional liquid handling apparatus 706 having a robotics unit configured for automated DNA extraction. Liquid handling apparatus 706 may be configured to handle multiple tube sizes and/or multiple sample types. For example, liquid handling apparatus 706 may be configured to handle either a 4 mm tube size or a 6 mm tube size. In another example, liquid handling apparatus 706 may be configured to handle either a blood sample or a saliva sample. In another embodiment, robotic system 700 includes a robotic refrigerator 707, which may be configured to store and retrieve sample plates of one or more different sizes. Robotic refrigerator 707 may be further configured, for example, to allow for human override to permit manual access to the contents within robotic refrigerator 707.

Figure 20:
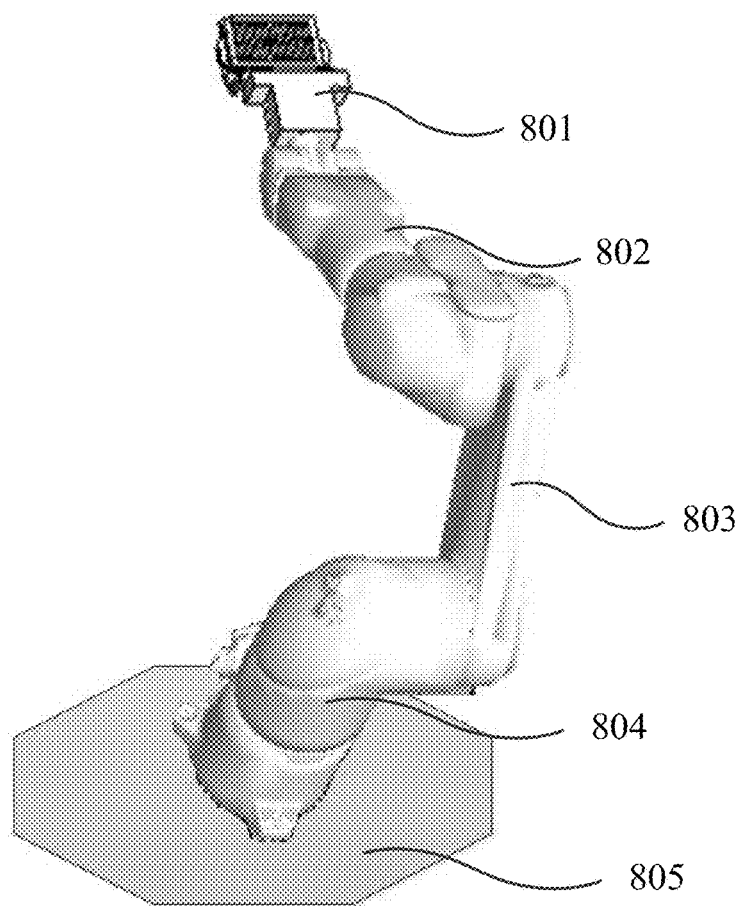
FIG. 20 illustrates an angled view of a robotic arm.

FIG. 20 illustrates an angled view of a robotic arm 800, for example, a robotic arm such as robotic arm 701 in FIG. 19. As depicted in FIG. 20, robotic arm 800 includes a sample handling portion 801, a first solid section 802, a second solid section 803, a third solid section 804, and a robotic arm base 805. In one embodiment, sample handling portion 801 is connected to the first solid section 802. In another embodiment, first solid section 802 is connected at one end to sample handling portion 801, and is connected at another end to second solid section 803. In yet another embodiment, second solid section 803 is connected at one end to first solid section 802, and is connected at another end to third solid section 804. In yet another embodiment, third solid section 804 is connected at one end to second solid section 803, and is connected at another end to robotic arm base 805.

The following examples are intended to illustrate but not limit the invention.

EXAMPLES

Example 1

Figure 12:
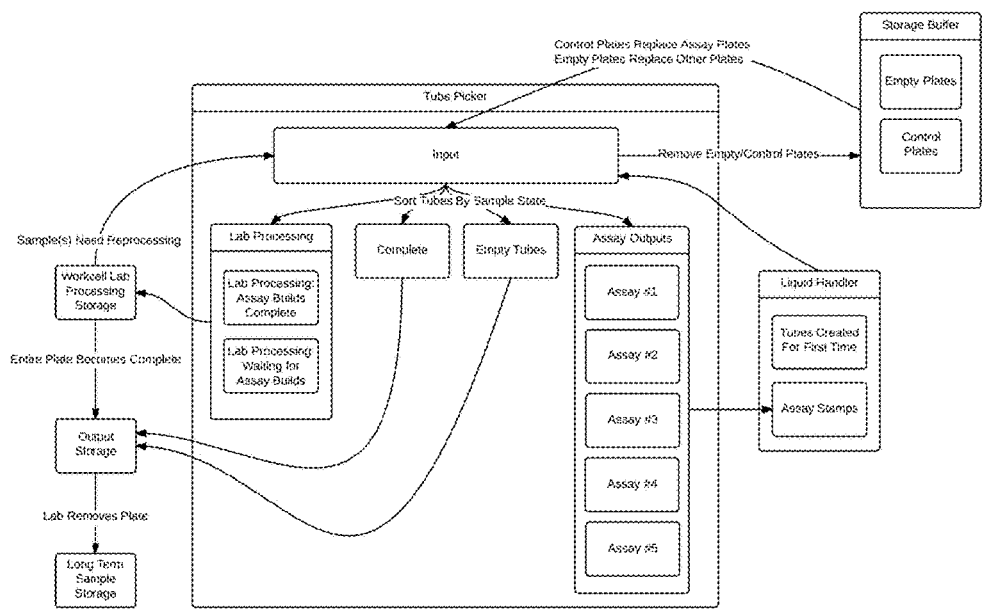
FIG. 12 shows an embodiment of a workflow for a sample sorting device as described herein.

An exemplary workflow for a sample sorting device as described herein is illustrated in FIG. 12.

Overview

The tube sorting workflow is a process for sorting tubes by tube state using a robotic sample sorting device as described herein. The sorting device takes in sample tube racks (plates) that are unsorted and outputs full plates ready for the next step. Unsorted plates can have any number of tubes and any combination of tube states.

Sample Tube States

1. No sample (empty tube)
2. Sample required for one or more assays. The assay with the highest priority is its current state.
3. Sample required for one or more assays, but those assays are unknown. This state represents pending more information.
4. Sample has completed all assays, but the assays are still being processed. These samples are kept in the workflow in case they need to be reprocessed.
5. Sample has completed all assays and all the assays have completed processing. These samples can be removed from the workflow.
6. Tube contains a "control" sample. Controls are kept in the unsorted plate, which becomes a control plate after the rest of the tubes are sorted.

Unsorted Plates Examples

Plates that are entering the workflow for the first time.
Plates that complete assay builds
Plates in a processing state (states 3, 4) where the samples change state and need to be reprocessed
Any other plate can be sorted Deck Locations The sample sorting device has as many "nest" locations to hold plates as there are sample states, plus the input unsorted plate. The number of sample states can vary based on the number of desired assays in the workflow.

Locations that are not assay locations (states 1, 3, 4, 5, 6) start out as empty plates. When the plates fill up, they are moved to their next location and are replaced with an empty plate.

Locations that are assay locations (state 2) start out either as empty plates or control plates, depending on if the assay needs controls. When these plates fill up, they are moved to their next location and are replaced with an empty plate.

Outputs

When the sample sorting device fills up plates, they move onto their next location.

Plates full of empty tubes and completed samples are moved to an output location to be removed from the workflow.

Plates full of processing samples (states 3, 4) are moved to a storage location within the workcell. They wait until one or more of the samples change to a processing state. If this happens, the plate is unsorted and goes through the sorting device. If all of the samples become complete, the plate is moved to an output location (bypassing the sorting device).

Plates from the assay states are moved to a liquid handler that builds the assay. After the liquid handling operation, the plate is unsorted and goes through the sorting device.

Buffers

The workflow requires that there are both empty plates and control plates in a buffer location for the sorting device. There must be as many empty plates as there are sorting device deck locations that start as empty plates. There must be control plates for each assay that requires control plates. The number of control plates required depends on the quantity of samples that are processed for that assay, but there should be multiple control plates for each assay.

As used herein, the terminology as used throughout the description of the invention is for the purpose of describing particular embodiments only. Such terminology does not limit the scope of the invention in any way. For example, singular forms of "a," "an" and "the" are intended to include plural forms unless indicated otherwise. Furthermore, terms such as "comprises" or "comprising" specify the presence of indicated features, components, steps, etc., but do not preclude the presence or addition of one or more other features, components, steps, etc. The description may also include the term "in," which may include "in" and "on" unless clearly indicated otherwise. Furthermore, usage of the term "or" includes both conjunctive and disjunctive meanings, unless clearly indicated otherwise. That is, unless expressly stated otherwise, the term "or" may include "and/or."

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A device for sorting sample tubes, comprising:
a robotic assembly, comprising: a base that comprises a vertical lift shaft; a horizontal robotic arm comprising a proximal end and a distal end, wherein the proximal end of the robotic arm is configured to be lifted vertically by the lift shaft and is configured for pivotal movement around the base; and end of arm tooling at the distal end of the robotic arm that is configured to pick up and hold a sample tube when a vacuum is applied and to expel and deposit the sample tube into a designated slot in a tube rack when air is expelled through the tooling;
a vacuum source that is fluidly connected to the end of arm tooling and configured to pull a vacuum through the tooling;
an air source that is fluidly connected to the end of arm tooling and configured to expel air through the tooling;
a horizontal stage underneath the robotic arm and configured to hold a plurality of tube racks in a position from which the end of arm tooling may pick up and deposit sample tubes;
a vision system that is configured to record coded information on sample tubes and on the sides of tube racks in the device and to convey the coded information to a control system; and
a control system that tracks coded information provided by the vision system, and that controls the robotic assembly to pick up a coded sample tube from a first location in a first tube rack and to deposit the sample tube in a second location in a second tube rack, wherein the first tube rack and the second tube rack are the same or different,
wherein the end of arm tooling comprises:
an open column comprising a top and a bottom, extending through at least a portion of the interior of the tooling and through which a suction force is applied via the vacuum source and air is expelled via the air source;
a first fitting that is connected to the top of the column and that is fluidly connected to the vacuum source and to the air source;
an adaptor at the bottom of the column that is of a dimension suitable to connect with and retain the top of a sample tube by suction when a vacuum is applied;
an open chamber comprising a top and a bottom, located within an upper portion of the tooling, wherein the chamber surrounds the first fitting; and
a second fitting that is fluidly connected to the air source and through which air passes into the top of the chamber when air pressure is applied,
wherein the bottom of the chamber comprises a plurality of openings through which air passes when air pressure is applied, said openings extending through a lower portion of the tooling and configured to expel air through the bottom of the tooling when the device is in operation.

2. A device according to claim 1, wherein the robotic arm is a Selective Compliance Assembly Robot Arm (SCARA), comprising:
a first horizontal arm segment comprising: a first proximal end that is configured to be lifted by the lift shaft and is configured for pivotal movement around the base, and a first distal end;
a second horizontal arm segment comprising: a second proximal end that is rotatably coupled to the first distal end, and a second distal end;
a third horizontal arm segment comprising: a third proximal end that is rotatably coupled to the second distal end, and a third distal end; and
the end of arm tooling connected to the third distal end.

3. A device according to claim 1, wherein the vacuum source and air source run simultaneously, wherein a vacuum is pulled through the end of arm tooling through the open column when a sample tube is picked up, wherein the vacuum is shut off when the sample tube is above a desired location in a tube rack, and wherein air is expelled briefly through the column after the vacuum is shut off, depositing the sample tube into the desired location in the tube rack.

4. A device according to claim 1, wherein the coded information comprises one-dimensional, two-dimensional, or three-dimensional bar codes on sample tubes and/or on tube racks.

5. A device according to claim 1, comprising at least one sample tube rack that comprises sample tubes, and wherein each sample tube in the rack comprises unique coded information on the bottom of the tube, wherein the tube rack comprises openings such that the coded information on the sample tubes is viewable through the bottom of the tube rack, wherein the vision system is configured beneath the bottom of the tube rack, and wherein the vision system records the locations of coded information when the tube rack is positioned above the vision system.

6. A device according to claim 1, comprising at least one sample tube rack that comprises unique coded information on at least one side, wherein the sample tube rack and the vision system are configured such that the coded information is recorded by the vision system when the tube rack is positioned above the vision system.

7. A device according to claim 1, comprising a sample tube rack comprising a plurality of sample tubes to be sorted, wherein each sample tube comprises a top and a bottom, wherein the top of the tube is configured and of a dimension such that the tube will be held by suction when picked up by the end of arm tooling of the robotic arm when a vacuum is applied therethrough, and wherein each sample tube comprises unique coded information on the bottom of the tube, wherein the vision system is configured to read and convey information about the locations of the coded information to the control system before and after sorting to desired locations in one or more tube rack.

8. A device according to claim 1, wherein the vacuum source and the air source are produced with a vacuum pump that creates a vacuum through the venturi effect, wherein a vacuum is produced when compressed air flows through a venturi, and wherein positive air pressure is produced when the flow of compressed air is terminated.

9. A device according to claim 1, further comprising a tube sensor that senses whether a sample tube has been picked up by the end of arm tooling when the vacuum is applied.

10. A device according to claim 1, wherein the stage is in the form of a deck or a track on a conveyer belt.

11. A device according to claim 1, wherein the device is configured to sort 20 or more sample tubes per minute.

12. A device according to claim 1, further comprising a plurality of sample tubes in one or more tube racks, wherein each sample tube comprises a unique identification code that may be read by the vision system and conveyed to the control system.

13. A device according to claim 12, comprising a plurality of tube racks, wherein each tube rack comprises a unique identification code that may be read by the vision system and conveyed to the control system.

14. A device according to claim 1, wherein said plurality of openings is a ring of openings around the open column that extends through the interior of the tooling and are configured to expel air around a sample tube, preventing interference from surrounding tubes in the tube rack, if any, when the robotic arm picks up the sample tube.

15. A device according to claim 14, wherein the ring of openings is disposed in a substantially circular configuration around the open column, and wherein the ring of openings is configured to expel air in a substantially circular configuration around a sample tube.

16. A device according to claim 1, wherein the vision system comprises three vision camera systems that are aligned to read coded information from a sample tube or sample tube rack when it is located in a position above the vision system.

17. A device according to claim 16, comprising a vision system under each location on the stage on which a sample tube rack may be positioned.

18. A device according to claim 16, comprising a single vision system, and comprising a track to move sample tube racks into position above the vision system for reading of coded information on sample tubes and/or on the tube rack.

19. A device according to claim 1, wherein the control system comprises a laboratory information management system (LIMS).

20. A method for sorting sample tubes, comprising a device according to claim 1, and further comprising at least one sample tube rack that comprises sample tubes, wherein a sample tube in a first location is sorted to a second location on the same or different sample tube rack, said method comprising:
 (a) moving the robotic arm via the control system to configure the end of arm tooling above the first location,
 (b) applying a vacuum via the vacuum source, thereby providing a suction force through the end of arm tooling, wherein the sample tube is picked up from the first location and retained by the end of arm tooling via vacuum suction,
 (c) moving the robotic arm via the control system to configure the end of arm tooling with the retained sample tube above the second location,
 (d) terminating the vacuum and applying positive air pressure through the end of arm tooling to expel the sample tube in the second location, and
 (e) determining the presence of the sample tube in the first location and/or second location by reading of coded information on the sample tube by the vision system.

21. A method according to claim 20, wherein the control system lowers the robotic arm before the sample tube is picked up, raises the robotic arm when it is moved to configure the end of arm tooling above the second location, and lowers the robotic arm before the sample tube is expelled in the second location.

22. A method according to claim 20, wherein the robotic arm is a SCARA, comprising:
 a first horizontal arm segment comprising: a first proximal end that is configured to be lifted by the lift shaft and is configured for pivotal movement around the base, and a first distal end;
 a second horizontal arm segment comprising: a second proximal end that is rotatably coupled to the first distal end, and a second distal end;
 a third horizontal arm segment comprising: a third proximal end that is rotatably coupled to the second distal end, and a third distal end; and
 the end of arm tooling connected to the third distal end.

23. A method according to claim 20, wherein the vacuum source and air source run simultaneously, wherein a vacuum is pulled through the end of arm tooling through the open column when a sample tube is picked up, wherein the vacuum is shut off when the sample tube is above a desired location in a tube rack, and wherein air is expelled briefly through the column after the vacuum is shut off, depositing the sample tube into the desired location in the tube rack.

24. A method according to claim 20, wherein the vacuum source and the air source are produced with a vacuum pump that creates a vacuum through the venturi effect, wherein a vacuum is produced when compressed air flows through a venturi, providing a suction force whereby the sample tube is picked up from the first location, and wherein positive air pressure is produced when the flow of compressed air is terminated, thereby expelling the sample tube in the second location.

25. A method according to claim 20, wherein the coded information comprises one-dimensional, two-dimensional, or three-dimensional bar codes on sample tubes and/or on sample racks.

26. A method according to claim 20, wherein each sample tube in the tube rack comprises unique coded information on the bottom of the tube, wherein the tube rack comprises openings such that the coded information on the sample tubes is viewable through the bottom of the tube rack, wherein the vision system is configured beneath the bottom of the tube rack, and wherein the vision system records the locations of coded information when the tube rack is positioned above the vision system.

27. A method according to claim 20, wherein each sample tube rack comprises unique coded information on at least one side, wherein the sample tube rack and the vision system are configured such that the coded information is recorded by the vision system when the tube rack is positioned above the vision system.

28. A method according to claim 20, wherein the vision system comprises three vision camera systems that are aligned to read coded information from a sample tube or sample tube rack when it is located in a position above the vision system.

29. A method according to claim 20, wherein the device further comprises a tube sensor that senses whether a sample tube has been picked up by the end of arm tooling when the vacuum is applied.

30. A method according to claim 20, wherein 20 or more sample tubes per minute are sorted.

31. A method according to claim 20, wherein said plurality of openings is a ring of openings around the open column that extends through the interior of the tooling, wherein air is expelled around a sample tube, preventing interference from surrounding tubes in the tube rack, if any, when the robotic arm picks up the sample tube.

32. A method according to claim 31, wherein the ring of openings is disposed in a substantially circular configuration about the open column, and wherein air is expelled in a substantially circular configuration around the sample tube.

* * * * *